(12) United States Patent
Drăghici

(10) Patent No.: US 8,068,994 B2
(45) Date of Patent: Nov. 29, 2011

(54) METHOD FOR ANALYZING BIOLOGICAL NETWORKS

(75) Inventor: Sorin Drăghici, Detroit, MI (US)

(73) Assignee: Wayne State University, Detroit, MI (US)

( * ) Notice: Subject to any disclaimer, the term of this patent is extended or adjusted under 35 U.S.C. 154(b) by 492 days.

(21) Appl. No.: 12/180,303

(22) Filed: Jul. 25, 2008

(65) Prior Publication Data

US 2009/0182513 A1 Jul. 16, 2009

Related U.S. Application Data

(60) Provisional application No. 60/952,354, filed on Jul. 27, 2007.

(51) Int. Cl.
*G06F 19/00* (2011.01)

(52) U.S. Cl. ............... 702/19; 702/20; 435/5; 435/6; 600/300; 703/11

(58) Field of Classification Search ............... 702/19, 702/20; 435/5, 6; 600/300; 703/11
See application file for complete search history.

(56) References Cited

U.S. PATENT DOCUMENTS

| | | | |
|---|---|---|---|
| 2005/0154535 A1* | 7/2005 | Sun et al. | 702/19 |
| 2005/0165594 A1* | 7/2005 | Chandra et al. | 703/11 |
| 2007/0059685 A1* | 3/2007 | Kohne | 435/5 |
| 2008/0254447 A1* | 10/2008 | Foekens et al. | 435/6 |
| 2008/0307537 A1* | 12/2008 | Bachoo | 800/18 |
| 2009/0313189 A1* | 12/2009 | Sun et al. | 706/12 |
| 2010/0057368 A1* | 3/2010 | Afeyan et al. | 702/19 |
| 2010/0086935 A1* | 4/2010 | Bevilacqua et al. | 435/6 |

* cited by examiner

*Primary Examiner* — Carol S Tsai
(74) *Attorney, Agent, or Firm* — Harness, Dickey & Pierce, P.L.C.

(57) ABSTRACT

Significance of biological pathway in disease state is predicted by (a) providing expression level data for a plurality of biomolecules differentially expressed in a disease state, compared with same biomolecules expressed in a non-diseased state: (b) determining presence probability of the biomolecules in disease state; (c) determining effect of each biomolecule from the plurality of biomolecules on the expression of different downstream biomolecules within pathway to provide perturbation factor for each biomolecule in the pathway; (d) combining statistical significance of differentially expressed biomolecules present in the disease state, with a sum of perturbation factors for all of the biomolecules, generating an impact factor; (e) calculating statistical significance of impact factor based upon determined probability of having statistical significant presence of differentially expressed biomolecules in step (b) and the sum of perturbation factors in step (c); and (f) outputting statistical significance of impact factor for the pathway relevant to the disease.

Figure 1A:
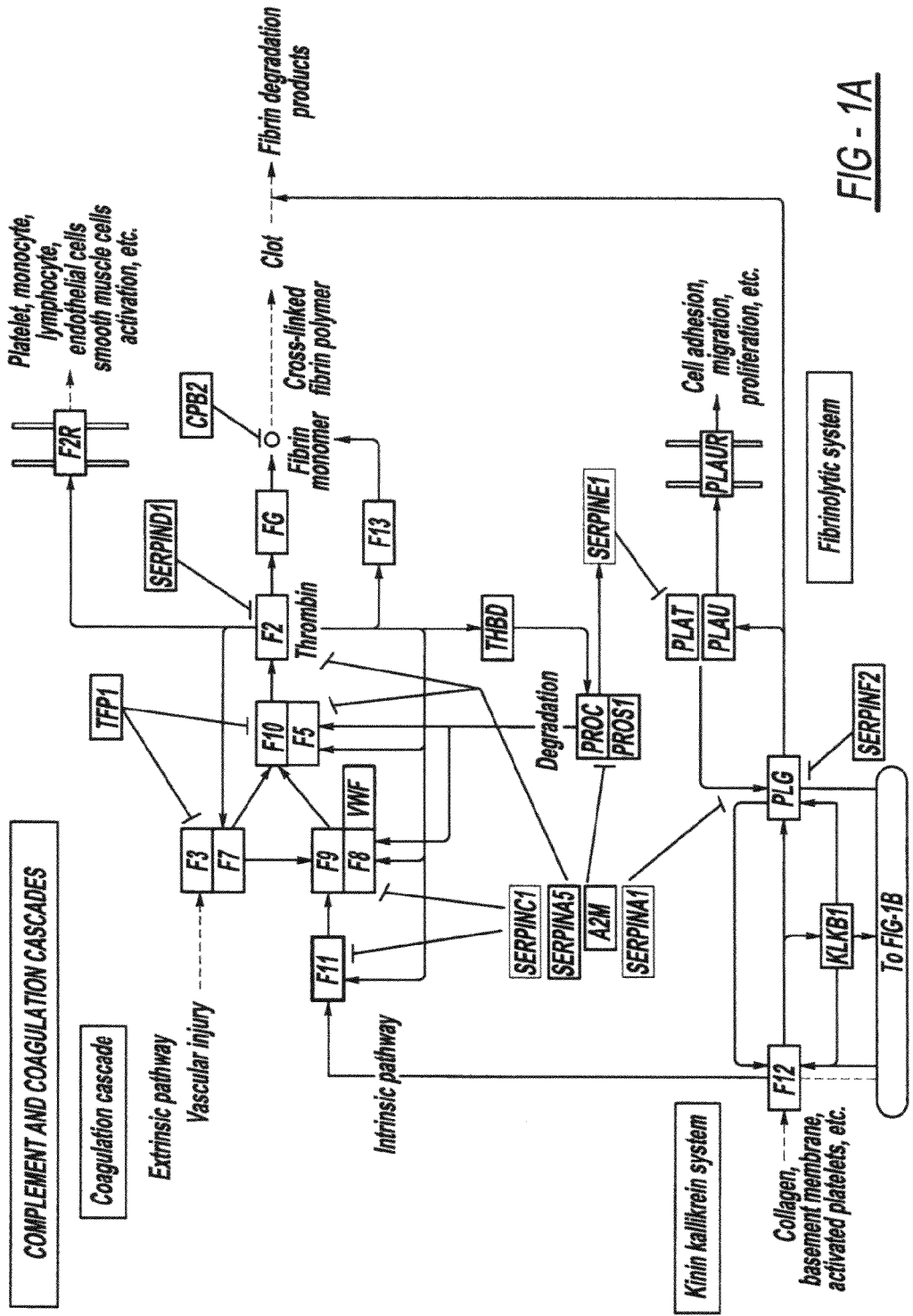

3 Claims, 23 Drawing Sheets
(3 of 23 Drawing Sheet(s) Filed in Color)

| Pathway name | ORA (hypergeometric) | | |
|---|---|---|---|
| | p-value | FDR | Bonferroni |
| Prion disease | 0.149649 | 0.627132 | 1 |
| Focal adhesion | 0.155424 | 0.627132 | 1 |
| Parkinson's disease | 0.164842 | 0.627132 | 1 |
| Dentatorubropallidoluysian atrophy | 0.179767 | 0.627132 | 1 |
| Calcium signaling pathway | 0.262884 | 0.627132 | 1 |
| Alzheimer's disease | 0.277100 | 0.627132 | 1 |
| Apoptosis | 0.283744 | 0.627132 | 1 |
| TGFbeta signaling pathway | 0.303663 | 0.627132 | 1 |
| Huntington's disease | 0.327491 | 0.627132 | 1 |
| Toll-like receptor signaling pathway | 0.330069 | 0.627132 | 1 |
| Wnt signaling pathway | 0.369145 | 0.637613 | 1 |
| Regulation of actin cytoskeleton | 0.439390 | 0.695701 | 1 |
| MAPK signaling pathway | 0.560814 | 0.762988 | 1 |
| Phosphatidylinositol signaling system | 0.572396 | 0.762988 | 1 |
| Adherens junction | 0.602359 | 0.762988 | 1 |
| Complement and coagulation cascades | 0.680333 | 0.766820 | 1 |
| Cell cycle | 0.686102 | 0.766820 | 1 |
| Cytokine-cytokine receptor interaction | 0.820650 | 0.866242 | 1 |
| Neuroactive ligand-receptor interaction | 0.972996 | 0.972996 | 1 |

*FIG-2A*

Enriched in cancer

| Pathway Name | NOM p-val | FDR q-val | FWER p-val (a) |
|---|---|---|---|
| Cell cycle | 0.038 | 0.118 | 0.140 |
| Huntington's disease | 0.074 | 0.217 | 0.546 |
| Dentatorubropallidoluysian atrophy (DRPLA) | 0.149 | 0.291 | 0.751 |
| Alzheimer's disease | 0.189 | 0.344 | 0.877 |
| Parkinson's disease | 0.373 | 0.485 | 0.984 |
| Adherens junction | 0.583 | 0.651 | 0.998 |
| Wnt signaling pathway | 0.861 | 0.785 | 1 |

Enriched in normal

| Pathway Name | NOM p-val | FDR q-val | FWER p-val (a) |
|---|---|---|---|
| MAPK signaling pathway | 0.007 | 0.170 | 0.361 |
| Apoptosis | 0.019 | 0.175 | 0.304 |
| Complement and coagulation cascades | 0.037 | 0.255 | 0.298 |
| Phosphatidylinositol signaling system | 0.189 | 0.343 | 0.823 |
| Regulation of actin cytoskeleton | 0.010 | 0.356 | 0.223 |
| Focal adhesion | 0.160 | 0.384 | 0.817 |
| Cytokine-cytokine receptor interaction | 0.241 | 0.420 | 0.910 |
| Toll-like receptor signaling pathway | 0.330 | 0.451 | 0.963 |
| Calcium signaling pathway | 0.308 | 0.489 | 0.960 |
| Prion disease | 0.474 | 0.563 | 0.986 |
| TGF beta signaling pathway | 0.631 | 0.699 | 0.998 |
| Neuroactive ligand-receptor interaction | 0.947 | 0.957 | 1 |

FIG-2B

| Pathway name | Impact Factor | | | |
|---|---|---|---|---|
| | IF | p-value | FDR | Bonferroni |
| Cell cycle | 19.26 | 8.76E-08 | 1.66E-06 | 1.66E-006 (a) |
| Focal adhesion | 7.414 | 0.005072 | 0.048180 | 0.0956831 |
| Wnt signaling pathway | 6.780 | 0.008840 | 0.055988 | 0.1679642 (a) |
| Dentatorubropallidoluysian atrophy | 5.535 | 0.025788 | 0.122495 | 0.4899810 (a) |
| Huntington's disease (b) | 4.543 | 0.058985 | 0.203925 | 1 |
| Apoptosis | 4.407 | 0.065921 | 0.203925 | 1 |
| Regulation of actin cytoskeleton | 4.246 | 0.075130 | 0.203925 | 1 |
| TGFbeta signaling pathway | 3.511 | 0.134730 | 0.319984 | 1 |
| Complement and coagulation cascades | 3.161 | 0.176357 | 0.354145 | 1 |
| Adherens junction | 2.953 | 0.206279 | 0.354145 | 1 |
| Alzheimer's disease (b) | 2.752 | 0.239378 | 0.354145 | 1 |
| Parkinson's disease (b) | 2.631 | 0.261455 | 0.354145 | 1 |
| Toll-like receptor signaling pathway | 2.576 | 0.272054 | 0.354145 | 1 |
| Prion disease (b) | 2.572 | 0.272839 | 0.354145 | 1 |
| Calcium signaling pathway (b) | 2.538 | 0.279588 | 0.354145 | 1 |
| Cytokine-cytokine receptor interaction | 2.353 | 0.318815 | 0.366952 | 1 |
| Phosphatidylinositol signaling system | 2.311 | 0.328326 | 0.366952 | 1 |
| MAPK signaling pathway | 2.205 | 0.353353 | 0.372984 | 1 |
| Neuroactive ligand-receptor interaction | 0.576 | 0.885936 | 0.885936 | 1 |

FIG-2C

| Pathway name | ORA (hypergeometric) | | |
|---|---|---|---|
| | p-value | FDR | Bonferroni |
| Cell cycle | 3.1E-07 | 2.8E-06 | 2.765E-06 |
| MAPK signaling pathway | 0.02513 | 0.11309 | 0.2261834 |
| Parkinson's disease. | 0.10752 | 0.32255 | 0.9676532 |
| Cytokine -cytokine receptor interaction | 0.24736 | 0.47992 | 1 |
| Focal adhesion | 0.29628 | 0.47992 | 1 |
| Calcium signaling pathway | 0.37158 | 0.47992 | 1 |
| Regulation of Actin cytoskeleton | 0.40691 | 0.47992 | 1 |
| TGF beta signaling pathway | 0.42660 | 0.47992 | 1 |
| Neuroactive ligand -receptor interaction | 0.58749 | 0.58749 | 1 |

*FIG - 4A*

Enriched in poor prognosis

| Pathway Name | NOM p-val | FDR q-val | FWER p-val |
|---|---|---|---|
| Ubiquitin mediated proteolysis | 0.031 | 0.113 | 0.111 |
| Prion disease | 0.352 | 0.570 | 0.802 |
| Alzheimer's disease | 0.279 | 0.625 | 0.683 |
| Tight junction | 0.848 | 0.749 | 0.974 |
| Parkinson's disease | 0.638 | 0.795 | 0.958 |

(b)

Enriched in good prognosis

| Pathway Name | NOM p-val | FDR q-val | FWER p-val | |
|---|---|---|---|---|
| Notch signaling pathway | 0.082 | 0.277 | 0.636 | |
| Neuroactive ligand-receptor interaction | 0.050 | 0.280 | 0.542 | |
| Adherens junction | 0.136 | 0.400 | 0.829 | |
| Wnt signaling pathway | 0.058 | 0.410 | 0.534 | |
| Circadian rhythm | 0.078 | 0.582 | 0.960 | |
| Complement and coagulation cascades | 0.232 | 0.638 | 0.997 | |
| Apoptosis | 0.212 | 0.691 | 0.996 | (a) |
| MAPK signaling pathway | 0.046 | 0.693 | 0.479 | |
| Amyotrophic lateral sclerosis | 0.244 | 0.738 | 0.993 | |
| Jak-STAT signaling pathway | 0.913 | 0.952 | 1 | |
| Dentatorubropallidoluysian atrophy | 0.792 | 0.987 | 1 | |
| Cytokine-cytokine receptor interaction | 0.913 | 0.987 | 1 | |
| Calcium signaling pathway | 0.522 | 1 | 1 | (a) |
| Focal adhesion | 0.556 | 1 | 1 | |
| Regulation of actin cytoskeleton | 0.575 | 1 | 1 | |
| Phosphatidylinositol signaling system | 0.735 | 1 | 1 | (a) |
| TGF-beta signaling pathway | 0.815 | 1 | 1 | |
| Cell cycle | 0.859 | 1 | 1 | |
| Huntington's disease | 0.885 | 1 | 1 | (a) |

*FIG - 4B*

| Pathway name | Impact Factor | | | |
|---|---|---|---|---|
| | IF | p-value | FDR | Bonferroni |
| Cell cycle | 18.8 | 1.3E-07 | 1.2E-06 | 1.19E-006 (a) |
| Focal adhesion | 7.06 | 0.00692 | 0.03112 | 0.0622412 (a) |
| TGF-beta signaling pathway | 6.56 | 0.01075 | 0.03225 | 0.0967557 (a) |
| MAPK signaling pathway | 5.40 | 0.02886 | 0.06493 | 0.2597164 (a) |
| Regulation of actin cytoskeleton | 4.49 | 0.06180 | 0.11125 | 0.5562285 |
| Parkinson's disease (b) | 3.12 | 0.18207 | 0.23946 | 1 |
| Cytokine - cytokine receptor interaction | 3.09 | 0.18624 | 0.23946 | 1 |
| Neuroactive ligand - receptor interaction | 2.87 | 0.21942 | 0.24685 | 1 |
| Calcium signaling pathway | 2.44 | 0.30047 | 0.30047 | 1 |

FIG-4C

| Pathway name | ORA (hypergeometric) | | |
|---|---|---|---|
| | p-value | FDR | Bonferroni |
| Complement and coagulation cascades | 1.26958E-07 | 2.28525E-06 | 2.28525E-06 (a) |
| Focal adhesion | 4.03691E-05 | 0.000363322 | 0.000726643 |
| MAPK signaling pathway | 0.000523961 | 0.003143765 | 0.009431295 |
| TGF-beta signaling pathway | 0.011698758 | 0.052644412 | 0.210577648 (a) |
| Toll-like receptor signaling pathway | 0.018714569 | 0.067372448 | 0.336862241 |
| Calcium signaling pathway | 0.024575814 | 0.072600598 | 0.442364654 (a) |
| Tight junction | 0.028233566 | 0.072600598 | 0.508204185 |
| Wnt signaling pathway | 0.050174237 | 0.100857467 | 0.903136270 |
| (b) Phosphatidylinositol signaling system | 0.058285692 | 0.100857467 | 1 |
| Prion disease | 0.060516063 | 0.100857467 | 1 |
| Jak-STAT signaling pathway | 0.061635119 | 0.100857467 | 1 |
| Apoptosis | 0.106427143 | 0.146873866 | 1 |
| Cell cycle | 0.106427143 | 0.146873866 | 1 |
| (b) Regulation of actin cytoskeleton | 0.115415266 | 0.146873866 | 1 |
| Alzheimer's disease | 0.122394888 | 0.146873866 | 1 |
| Huntington's disease | 0.146968097 | 0.165339109 | 1 |
| (b) Neuroactive ligand - receptor interaction | 0.233787848 | 0.247540075 | 1 |
| Cytokine -cytokine receptor interaction | 0.429908167 | 0.429908167 | 1 |

*FIG - 5A*

| Pathway name | Impact Factor | | | |
|---|---|---|---|---|
| | IF | p - value | FDR | Bonferroni |
| Complement and coagulation cascades | 19.374 | 7.85335E-08 | 1.41360E-06 | 1.44761E-06 (a) |
| Focal adhesion | 13.791 | 1.51580E-05 | 1.36422E-04 | 3.01180E-04 (a) |
| MAPK signaling pathway | 9.475 | 8.03922E-04 | 0.004823531 | 0.014470593 (a) |
| Tight junction | 7.128 | 0.006521277 | 0.029345745 | 0.117382981 (a) |
| TGF-beta signaling pathway | 6.868 | 0.008187095 | 0.029473543 | 0.147367717 |
| Toll-like receptor signaling pathway | 6.391 | 0.012391594 | 0.037174781 | 0.223048688 |
| Calcium signaling pathway | 5.774 | 0.021048873 | 0.052496861 | 0.378879719 |
| Apoptosis | 5.653 | 0.023331938 | 0.052496861 | 0.419974887 |
| Regulation of actin cytoskeleton | 5.225 | 0.033492741 | 0.066985482 | 0.602869334 |
| Jak-STAT signaling pathway | 4.983 | 0.041004319 | 0.073807774 | 0.738077735 |
| Wnt signaling pathway | 4.313 | 0.071158653 | 0.116441431 | 1 |
| Phosphatidylinositol signaling system | 3.975 | 0.093427025 | 0.133344438 | 1 |
| Prion disease | 3.937 | 0.096304316 | 0.133344438 | 1 |
| Huntington's disease | 3.839 | 0.104111596 | 0.133857767 | 1 (b) |
| Alzheimer's disease | 3.387 | 0.148324272 | 0.171694058 | 1 (b) |
| Cell cycle | 3.350 | 0.152616940 | 0.171694058 | 1 (b) |
| Neuroactive ligand - receptor interaction | 2.414 | 0.305405348 | 0.323370368 | 1 |
| Cytokine - cytokine receptor interaction | 2.208 | 0.352624224 | 0.352624224 | 1 |

*FIG - 5B*

Figure 8A:
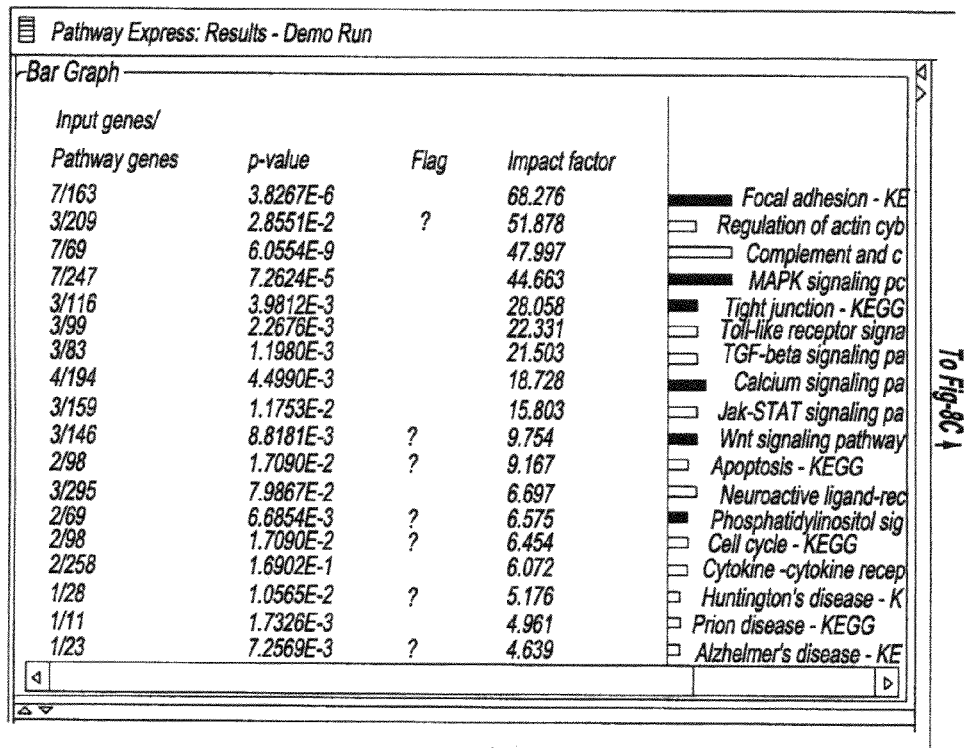

To Fig-8A

Input Details

Organism: Hs
Input type: GenBank accession
Input ids: 130
Gene symbols input ids mapped to: 129

| Input Id | Fold Change | #Pathways | Gene Symbol | Gene Na |
|---|---|---|---|---|
| H17173 | -2.0 | 0 | PCDHB15 | protocadherin beta 15 |
| R98321 | 1.9 | 0 | RNASE4 | ribonuclease, RNase A family, 4 |
| H49120 | -2.7 | 0 | DAPK3 | death-associated protein kinase 3 |
| T81425 | -1.7 | 0 | ATF5 | activating transcription factor 5 |
| AA156612 | -1.7 | 0 | GNB1 | guanine nucleotide binding protein (G |
| R70369 | 1.7 | 0 | GPX4 | glutathione peroxidase 4 (phospholip |
| AA031920 | -1.6 | 0 | CYBA | cytochrome b-245, alpha polypeptide |
| R89566 | 1.6 | 0 | TM7SF2 | transmembrane 7 superfamily memb |
| W56366 | 1.6 | 0 | VLDLR | very low density lipoprotein receptor |
| N95177 | -2.0 | 0 | RFC1 | replication factor C (activator 1) 1, 145 |
| AA099134 | -2.2 | 0 | HYOU1 | hypoxia up-regulated 1 |
| R34906 | -1.6 | 0 | IL1RN | interleukin 1 receptor antagonist |
| N24118 | -2.5 | 0 | IGFBP3 | Insulin-like growth factor binding prot |
| T98139 | 2.2 | 0 | HLA-B | major histocompatibility complex class |
| R25694 | -1.9 | 0 | EIF4G1 | eukaryotic translation initiation factor |
| AA156876 | -1.6 | 0 | TEAD3 | TEA domain family member 3 |
| W25479 | -1.7 | 0 | SOX4 | SRY (sex determining region Y) - box 4 |
| R96617 | 1.9 | 0 | ABCC2 | ATP-binding cassette, sub-family C (C |
| H03906 | -2.9 | 2 | FN1 | fibronectin 1 |
| R14058 | -2.8 | 6 | PRKCB1 | protein kinase C, beta 1 |
| N25636 | 1.6 | 0 | ESD | esterase D/formylglutathione hydrolase |
| R70035 | -1.6 | 2 | MYL6 | myosin, light polypeptide 6, alkali, sm |
| H89255 | -2.2 | 1 | LAMB1 | laminin, beta 1 |
| T86312 | 1.6 | 0 | FIBL-6 | hemicentin |
| W78787 | 2.0 | 1 | C5 | complement component 5 |
| R61634 | -1.8 | 0 | PRO1855 | hypothetical protein PRO1855 |

To Fig-8D

FIG - 8B

Pathway Details

Genes in current database 23543

| Rank | Database | Pathway Name | Impact Factor | #Genes in ... | #Input Gen | #Pathway G. | %input |
|---|---|---|---|---|---|---|---|
| 1 | KEGG | Focal adhesion | 68.276 | 163 | 7 | 163 | 5.426 |
| 2 | KEGG | Regulation of actin cytoskeleton | 51.878 | 209 | 3 | 209 | 2.326 |
| 3 | KEGG | Complement and coagulation cascades | 47.997 | 69 | 7 | 69 | 5.426 |
| 4 | KEGG | MAPK signaling pathway | 44.663 | 247 | 7 | 247 | 5.426 |
| 5 | KEGG | Tight junction | 28.058 | 116 | 3 | 116 | 2.326 |
| 6 | KEGG | Toll-like receptor signaling pathway | 22.331 | 99 | 3 | 99 | 2.326 |
| 7 | KEGG | TGF-beta signaling pathway | 21.503 | 83 | 3 | 83 | 2.326 |
| 8 | KEGG | Calcium signaling pathway | 18.728 | 194 | 4 | 194 | 3.101 |
| 9 | KEGG | Jak-STAT signaling pathway | 15.803 | 159 | 3 | 159 | 2.326 |
| 10 | KEGG | Wnt signaling pathway | 9.754 | 146 | 3 | 146 | 2.326 |
| 11 | KEGG | Apoptosis | 9.167 | 98 | 2 | 98 | 1.55 |
| 12 | KEGG | Neuroactive ligand-receptor interaction | 6.697 | 295 | 3 | 295 | 2.326 |
| 13 | KEGG | Phosphatidylinositol signaling system | 6.575 | 69 | 2 | 69 | 1.55 |
| 14 | KEGG | Cell cycle | 6.454 | 98 | 2 | 98 | 1.55 |
| 15 | KEGG | Cytokine-cytokine receptor interaction | 6.072 | 258 | 2 | 258 | 1.55 |
| 16 | KEGG | Huntington's disease | 5.176 | 28 | 1 | 28 | 0.775 |
| 17 | KEGG | Prion disease | 4.961 | 11 | 1 | 11 | 0.775 |
| 18 | KEGG | Alzheimer's disease | 4.639 | 23 | 1 | 23 | 0.775 |

FIG - 8C

FIG - 8D

Pathway Genes Details - Complement and coagulation cascades - KEGG

| Gene Symbol | Gene Name | Perturbatio | Fold Chan | Selected Pathway Genes List: |
|---|---|---|---|---|
| A2M | alpha-2-macroglobulin | 0.0 | 0.0 | A2M |
| BD |   |   |   | BDKRB1 |
| BD | Display Gene Info For |   |   | BDKRB2 |
| BF | Show in Pathway | 0.0 | 0.0 | BF |
| C1 | Add To Gene Selection List | All Pathway Genes |   | C1QA |
| C1 |   | All Input Genes in Pathway | 0.0 | C1QB |
| C1 | Save This table | All Non-Input Genes in Pathway | 0.0 | C1QG |
| C1R | complement compone | From Subselection | | 1R |
| C1S | complement compone | All Genes | | 1S |
| C2 | complement compone | Input Genes Only | | 2 |
| C3 | complement component 3 | 4.1 | 0.0 | 3 |
| C3AR1 | complement component 3a receptor 1 | 1.0 Non-Input Genes Only | | C3AR1 |
| C4A | complement component 4A | 0.0 | 0.0 | C4A |
| C4B | complement component 4B | 0.0 | 0.0 | C4B |
| C4BPA | complement component 4 binding protein, alpha | 0.0 | 0.0 | C4BPA |
| C4BPB | complement component 4 binding protein, beta | 0.0 | 0.0 | C4BPB |
| C5 | complement component 5 | 3.0299 | 2.0 | C5 |
| C5R1 | complement component 5 receptor 1 (C5a ligand) | 1.5149 | 0.0 | C5R1 |
| C6 | complement component 6 | 1.5149 | 0.0 | C6 |
| C7 | complement component 7 | 1.515 | 0.0 | C7 |
| C8A | complement component 8, alpha polypeptide | 0.505 | 0.0 | C8A |
| C8B | complement component 8, beta polypeptide | 0.505 | 0.0 | C8B |
| C8G | complement component 8, gamma polypeptide | 0.505 | 0.0 | C8G |
| C9 | complement component 9 | 1.5153 | 0.0 | C9 |
| CD59 | CD59 antigen p18-20 (antigen identified by monoclo. | 0.0 | 0.0 | CD59 |
| CFH | complement factor H | 0.0 | 0.0 | CFH |
| CPB2 | carboxypeptidase B2 (plasma, carboxypeptidase U) | 2.2 | 2.2 | CPB2 |
| CR1 | complement component (3b/4b) receptor 1, including | 1.0299 | 0.0 | CR1 |
| CR2 | complement component (3d/Epstein Barr virus rece. | 1.0299 | 0.0 | CR2 |
| DAF | decay accelerating factor for complement (CD55, Cr. | 0.0 | 0.0 |   |
| DF | D component of complement (adipsin) | 0.0 | 0.0 |   |

To Fig-8C
To Fig-8B

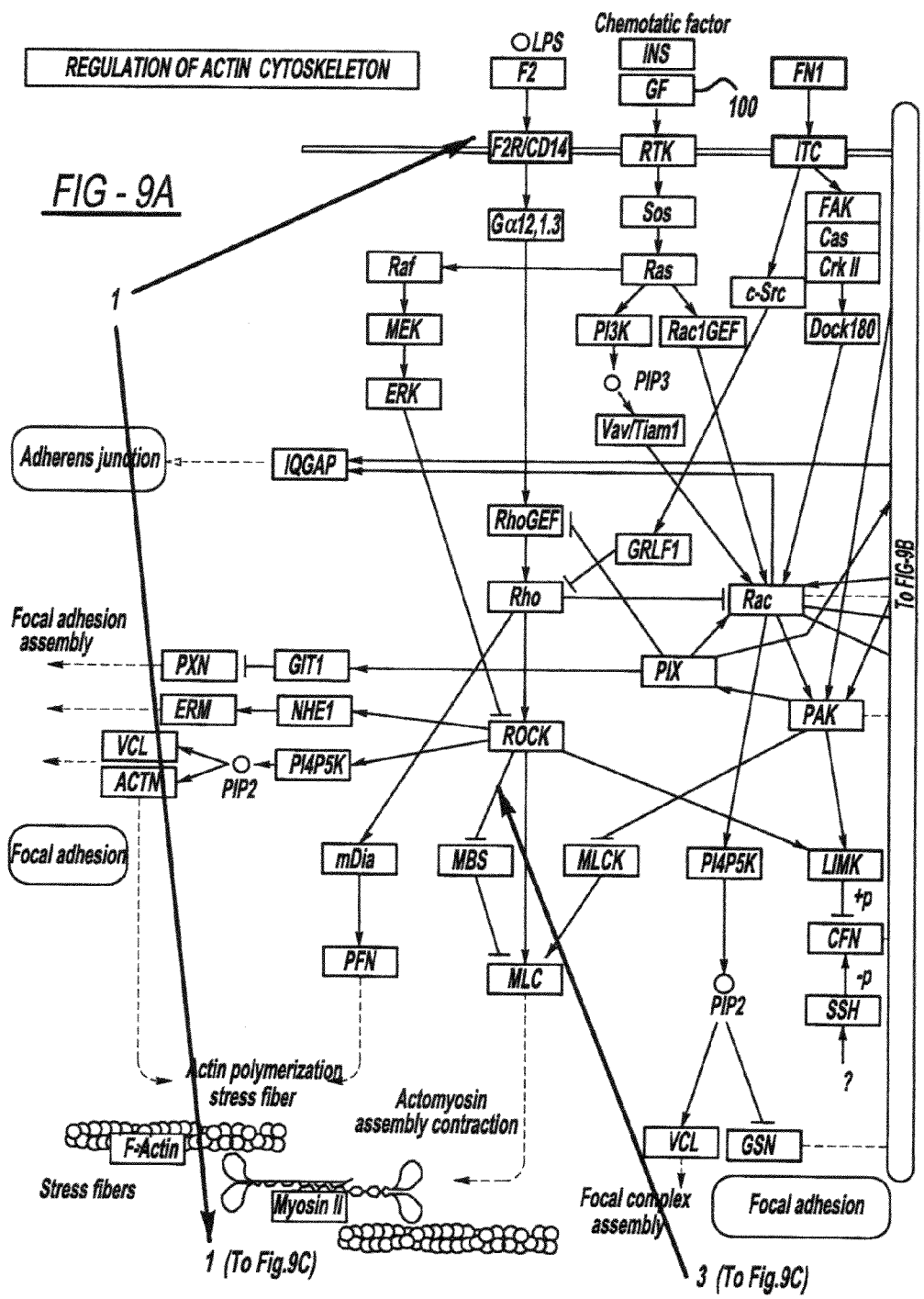

METHOD FOR ANALYZING BIOLOGICAL NETWORKS

CROSS-REFERENCE TO RELATED APPLICATIONS

This application claims the benefit of U.S. Provisional Application No. 60/952,354, filed on Jul. 27, 2007. The entire disclosure of the above application is incorporated herein by reference.

GOVERNMENT RIGHTS

This disclosure was made with government support under National Science Foundation, grant number 0234806, and National Institutes of Health, grant number 5R01HG003491-03. The Government has certain rights in the invention.

FIELD

The present disclosure relates to methods and systems for determining the significance and relevance of a particular biological pathway in a disease.

BACKGROUND

This section provides background information related to the present disclosure which is not necessarily prior art.

Together with the ability of generating a large amount of data per experiment, high throughput technologies also brought the challenge of translating such data into a better understanding of the underlying biological phenomena. Independent of the platform and the analysis methods used, the result of a high-throughput experiment is, in many cases, a list of differentially expressed genes. The common challenge faced by all researchers is to translate such lists of differentially expressed genes into a better understanding of the underlying biological phenomena and in particular, to put this in the context of the whole organism as a complex system. A computerized analysis approach using the Gene Ontology (GO) was proposed to deal with this issue. This approach takes a list of differentially expressed genes and uses a statistical analysis to identify the GO categories (e.g. biological processes, etc.) that are over- or under-represented in the condition under study. Given a set of differentially expressed genes, this approach compares the number of differentially expressed genes found in each category of interest with the number of genes expected to be found in the given category just by chance. If the observed number is substantially different from the one expected just by chance, the category is reported as significant. A statistical model (e.g. hypergeometric) can be used to calculate the probability of observing the actual number of genes just by chance, i.e., a p-value. Currently, there are over 20 tools using this over-representation approach (ORA). In spite of its wide adoption, this approach has a number of limitations related to the type, quality, and structure of the annotations available. An alternative approach considers the distribution of the pathway genes in the entire list of genes and performs a functional class scoring (FCS) which also allows adjustments for gene correlations. Arguably the state-of-the-art in the FCS category, the Gene Set Enrichment Analysis (GSEA), ranks all genes based on the correlation between their expression and the given phenotypes, and calculates a score that reflects the degree to which a given pathway P is represented at the extremes of the entire ranked list. The score is calculated by walking down the list of genes ordered by expression change. The score is increased for every gene that belongs to P and decreased for every gene that does not. Statistical significance is established with respect to a null distribution constructed by permutations.

Both ORA and FCS techniques currently used are limited by the fact that each functional category is analyzed independently without a unifying analysis at a pathway or system level. This approach is not well suited for a systems biology approach that aims to account for system level dependencies and interactions, as well as identify perturbations and modifications at the pathway or organism level. Several pathway databases such as KEGG, BioCarta, and Reactome, currently describe metabolic pathway and gene signaling networks offering the potential for a more complex and useful analysis. A recent technique, ScorePage, has been developed in an attempt to take advantage of this type of data for the analysis of metabolic pathways. Unfortunately, no such technique currently exists for the analysis of gene signaling networks. All pathway analysis tools currently available use one of the ORA approaches above and fail to take advantage of the much richer data contained in these resources. GenMAPP/MAPPfinder and GeneSifter use a standardized Z-score. PathwayProcessor, PathMAPA, Cytoscape and PathwayMiner use Fisher's exact test. MetaCore uses a hypergeometric model, while ArrayXPath offers both fisher's exact test and a false discovery rate (FDR). Finally, VitaPad and Pathway Studio focus on visualization alone and do not offer any analysis.

The approaches currently available for the analysis of gene signaling networks share a number of important limitations. Firstly, these approaches consider only the set of genes on any given pathway and ignore their position in those pathways. This may be unsatisfactory from a biological point of view. If a pathway is triggered by a single gene product or activated through a single receptor and if that particular protein is not produced, the pathway will be greatly impacted, probably completely shut off. If the insulin receptor (INSR) is not present, the entire pathway is shut off. Conversely, if several genes are involved in a pathway but they only appear somewhere downstream, changes in their expression levels may not affect the given pathway as much.

Secondly, some genes have multiple functions and are involved in several pathways but with different roles. For instance, the above INSR is also involved in the adherens junction pathway as one of the many receptor protein tyrosine kinases. However, if the expression of INSR changes, this pathway is not likely to be heavily perturbed because INSR is just one of many receptors on this pathway. Once again, all these aspects are not considered by any of the existing approaches.

Probably the most important challenge today is that the knowledge embedded in these pathways about how various genes interact with each other is not currently exploited. The very purpose of these pathway diagrams is to capture some of our knowledge about how genes interact and regulate each other. However, the existing analysis approaches consider only the sets of genes involved on these pathways, without taking into consideration their topology. In fact, our understanding of various pathways is expected to improve as more data is gathered. Pathways will be modified by adding, removing or re-directing links on the pathway diagrams. Most existing techniques are completely unable to even sense such changes. Thus, these techniques will provide identical results as long as the pathway diagram involves the same genes, even if the interactions between them are completely re-defined over time.

Finally, up to now the expression changes measured in these high throughput experiments have been used only to identify differentially expressed genes (ORA approaches) or to rank the genes (FCS methods), but not to estimate the impact of such changes on specific pathways. Thus, ORA techniques will see no difference between a situation in which a subset of genes is differentially expressed just above the detection threshold (e.g., 2 fold) and the situation in which the same genes are changing by many orders of magnitude (e.g., 100 fold). Similarly, FCS techniques can provide the same rankings for entire ranges of expression values, if the correlations between the genes and the phenotypes remain similar. Even though analyzing this type of information in a pathway and system context would be extremely meaningful from a biological perspective, currently there is no technique or tool able to do this.

We propose a radically different approach for pathway analysis that attempts to capture all aspects above. An impact factor (IF) is calculated for each pathway incorporating parameters such as the normalized fold change of the differentially expressed genes, the statistical significance of the set of pathway genes, and the topology of the signaling pathway. We show on a number of real data sets that the intrinsic limitations of the classical analysis produce both false positives and false negatives while the impact analysis provides biologically meaningful results.

SUMMARY

This section provides a general summary of the disclosure, and is not a comprehensive disclosure of its full scope or all of its features.

Methods, systems, computational processes and recordable media are provided for analyzing the significance of a pathway or network in a disease state. The methods comprise (a) providing data on the expression levels of a plurality of biomolecules differentially expressed in a disease state as compared with the same biomolecules expressed in a non-diseased state within the pathway: (b) determining the probability of the presence of the plurality of biomolecules in said diseased state; (c) determining the effect of each biomolecule from the plurality of biomolecules on the expression of different downstream biomolecules within the pathway thereby providing a perturbation factor for each biomolecule in the pathway; (d) combining the statistical significance of the differentially expressed biomolecule within the pathway present in the disease state with a sum of perturbation factors for all of the biomolecules in the pathway to generate an impact factor for the pathway relevant to the disease state; (e) calculating the statistical significance of the impact factor based upon a determined probability of having a statistical significant presence of differentially expressed biomolecules in step (b) and the sum of perturbation factors within the pathway in step (c); and (f) outputting the statistical significance of the impact factor for the pathway relevant to the disease for a user.

The systems, computational processes and recordable media including the methods for analyzing the significance of a pathway or network in a disease state can be used to tailor specific disease treatments that impact on pathway(s) that has been found to be of significant relevance in a particular disease. Moreover, specific drugs can be designed or synthesized that are effective for one or more biomolecules found in a pathway having a statistical significance in a particular disease state.

Further areas of applicability will become apparent from the description provided herein. The description and specific examples in this summary are intended for purposes of illustration only and are not intended to limit the scope of the present disclosure.

DRAWINGS

The patent or application file contains at least one drawing executed in color. Copies of this patent or patent application publication with color drawing(s) will be provided by the Office upon request and payment of the necessary fee.

The drawings described herein are for illustrative purposes only of selected embodiments and not all possible implementations, and are not intended to limit the scope of the present disclosure.

Figure 1B:
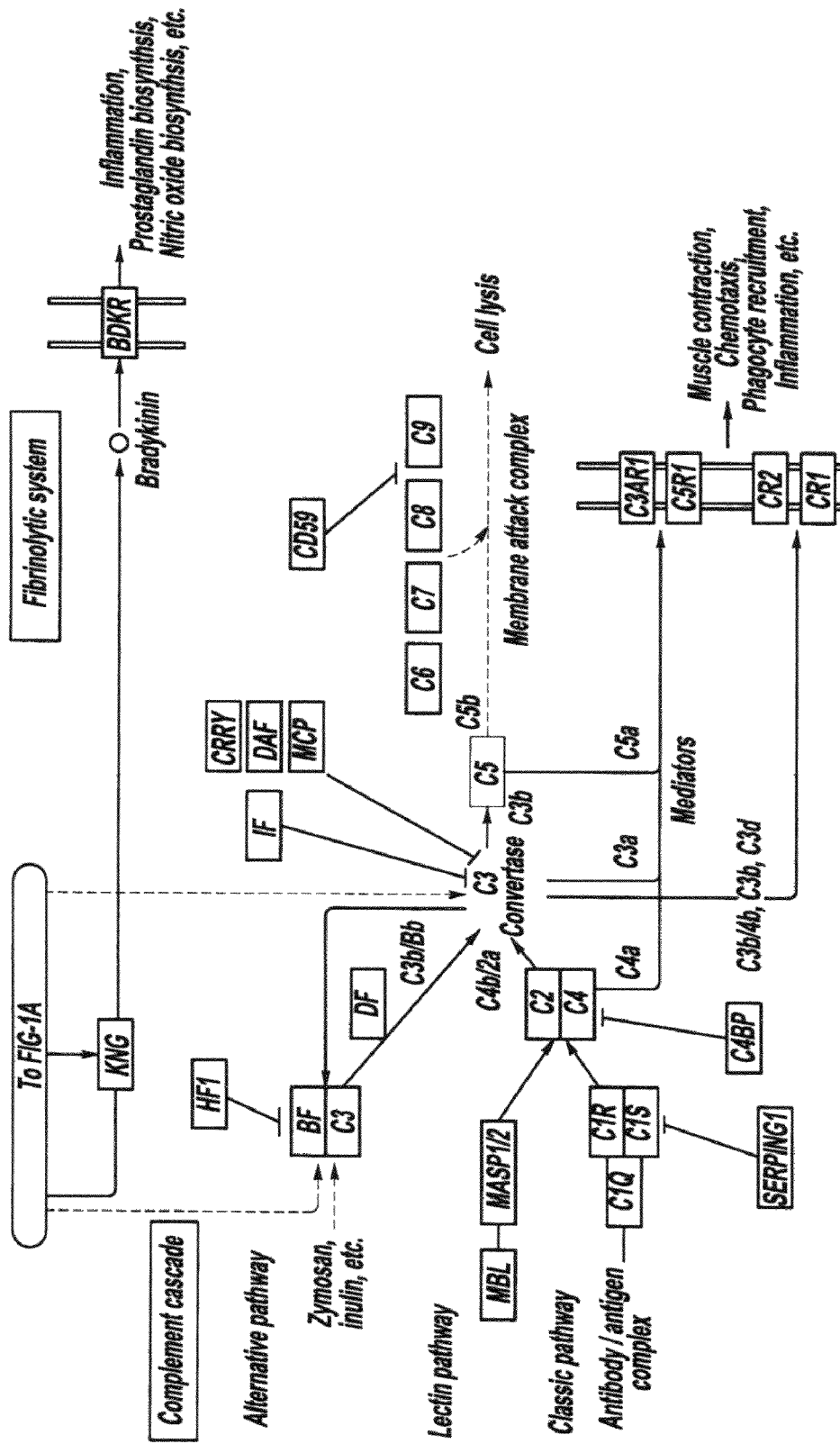

FIG. 1 (shown in the drawings as FIG. 1A and FIG. 1B) depicts the pathway Complement and Coagulation Cascades as affected by treatment with palmitate in a hepatic cell line. There are 7 differentially expressed genes out of 69 total genes. All classical ORA models would give any other pathway with the same proportion of genes a similar p-value, disregarding the fact that 6 out of these 7 genes are involved in the same region of the pathway, closely interacting with each other. Both ORA and GSEA would yield exactly the same significance value to this pathway even if the diagram were to be completely re-designed by future discoveries. In contrast, the impact factor can distinguish between this pathway and any other pathway with the same proportion of differentially expressed gene, as well as take into account any future chanaes to the topology of the pathway.

FIGS. 2A-2C depict a comparison between the results of the classical probabilistic approaches (FIG. 2A—over-representation approach (ORA) hypergeometric, FIG. 2B—Gene Set Enrichment Analysis (GSEA) and the results of the pathway impact analysis (FIG. 2C) for a set of genes differentially expressed in lung adenocarcinoma. In FIGS. 2A-2C, the pathways shaded in green are considered most likely to be linked to this condition in this experiment. The pathways shaded in orange are unlikely to be related. The ranking of the pathways produced by the classical approaches is very misleading. According to the hypergeometric model shown in FIG. 2A, the most significant pathways in this condition are: prion disease, focal adhesion, and Parkinson's disease. Two out of these 3 are likely to be incorrect. In FIG. 2B, GSEA yields cell cycle as the most enriched pathway in cancer but 3 out of the 4 subsequent pathways are clearly incorrect. In contrast, all 3 top pathways identified by the impact analysis are relevant to the given condition. The impact analysis is also superior from a statistical perspective. According to both hypergeometric and GSEA, no pathway is significant at the usual 1% or 5% levels on corrected p-values. In contrast, according to the impact analysis the cell cycle is significant at 1%, and focal adhesion and Wnt signaling are significant at 5% and 10%, respectively.

Figure 3A:
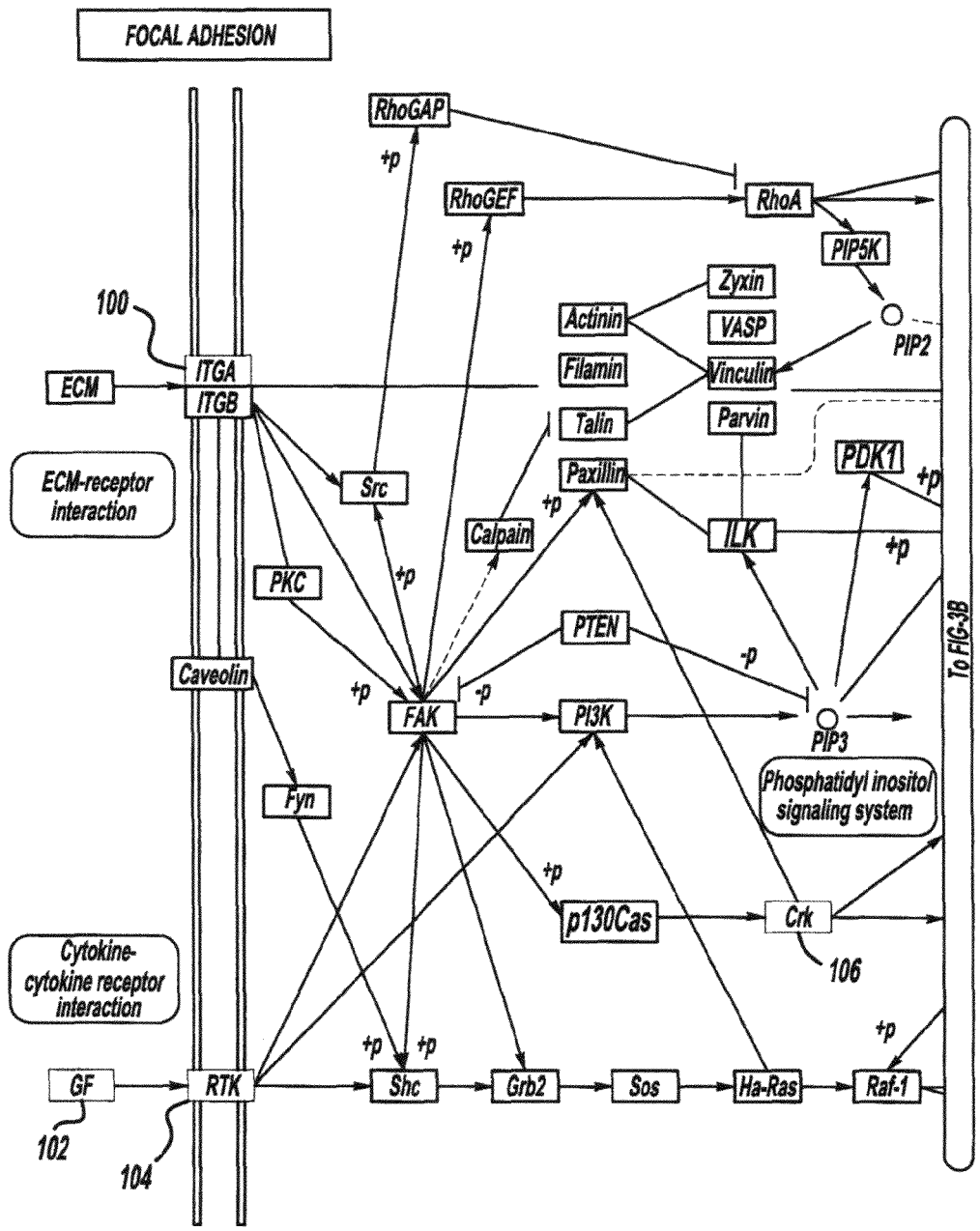
Figure 3B:
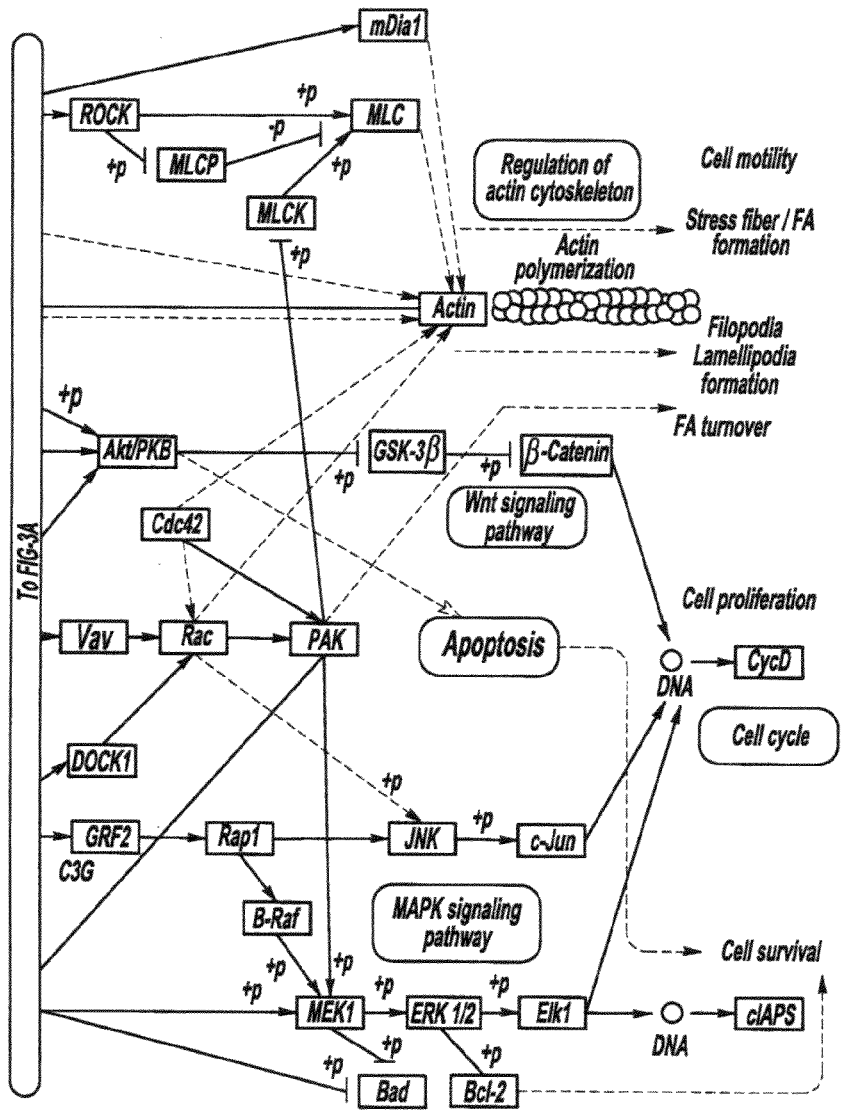

FIG. 3 depicts a focal adhesion pathway as impacted in lung adenocarcinoma vs. normal. In this condition, both ITG and RTK receptors are perturbed, as well as the VEGF ligand (the 3 genes shown in red). Because these 3 genes appear at the very beginning and affect both entry points controlling this pathway, their perturbations are widely propagated throughout the pathway and this pathway appears as highly impacted. All classical approaches completely ignore the positions of the genes on the given pathways and fail to identify this pathway as significant.

FIGS. 4A-4C depict a comparison between the results of the classical (ORA) probabilistic approach (FIG. 4A), GSEA (FIG. 4B) and the results of the pathway impact analysis (FIG. 4C) in tabular form for a set of genes associated with poor prognosis in breast cancer. The pathways shaded in green are well supported by the existing literature. The pathways shaded in orange are unlikely to be related. After correcting for multiple comparisons, GSEA shown in FIG. 4B fails to identify any pathway as significantly impacted in this condition at any of the usual significance levels (1%, 5% or 10%). The hypergeometric model shown in FIG. 4A pinpoints cell cycle as the only significant pathway. Relevant pathways such as focal adhesion, TGF-beta signaling, and MAPK do not appear as significant from a hypergeometric point of view. While agreeing on the cell cycle, the impact analysis shown in FIG. 4C also identifies the 3 other relevant pathways as significant at the 5% level.

FIGS. 5A-5B depict a comparison between the results of the classical probabilistic approach (FIG. 5A) and the results of the impact analysis (FIG. 5B) for a set of genes found to be differentially expressed in a hepatic cell line treated with palmitate in tabular form. Green shaded pathways are well supported by literature evidence while orange shaded pathways are unlikely to be relevant. The classical statistical analysis shown in FIG. 5A, yields 3 pathways significant at the 5% level: complement and coagulation cascades, focal adhesion and MAPK. The impact analysis shown in FIG. 5B agrees on these 3 pathways but also identifies several additional pathways. Among these, tight junction is well supported by the literature.

Figure 6A:
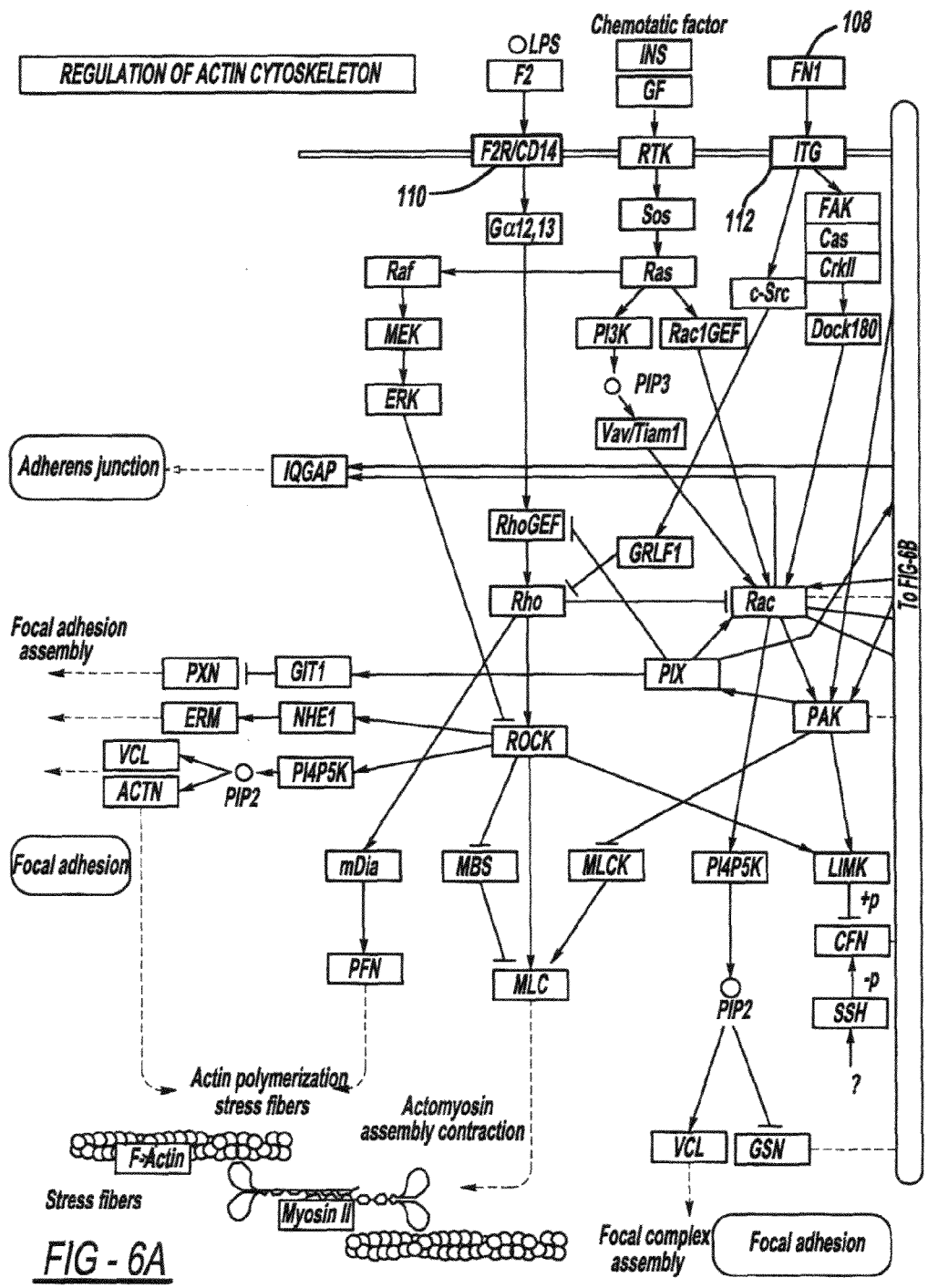
Figure 6B:
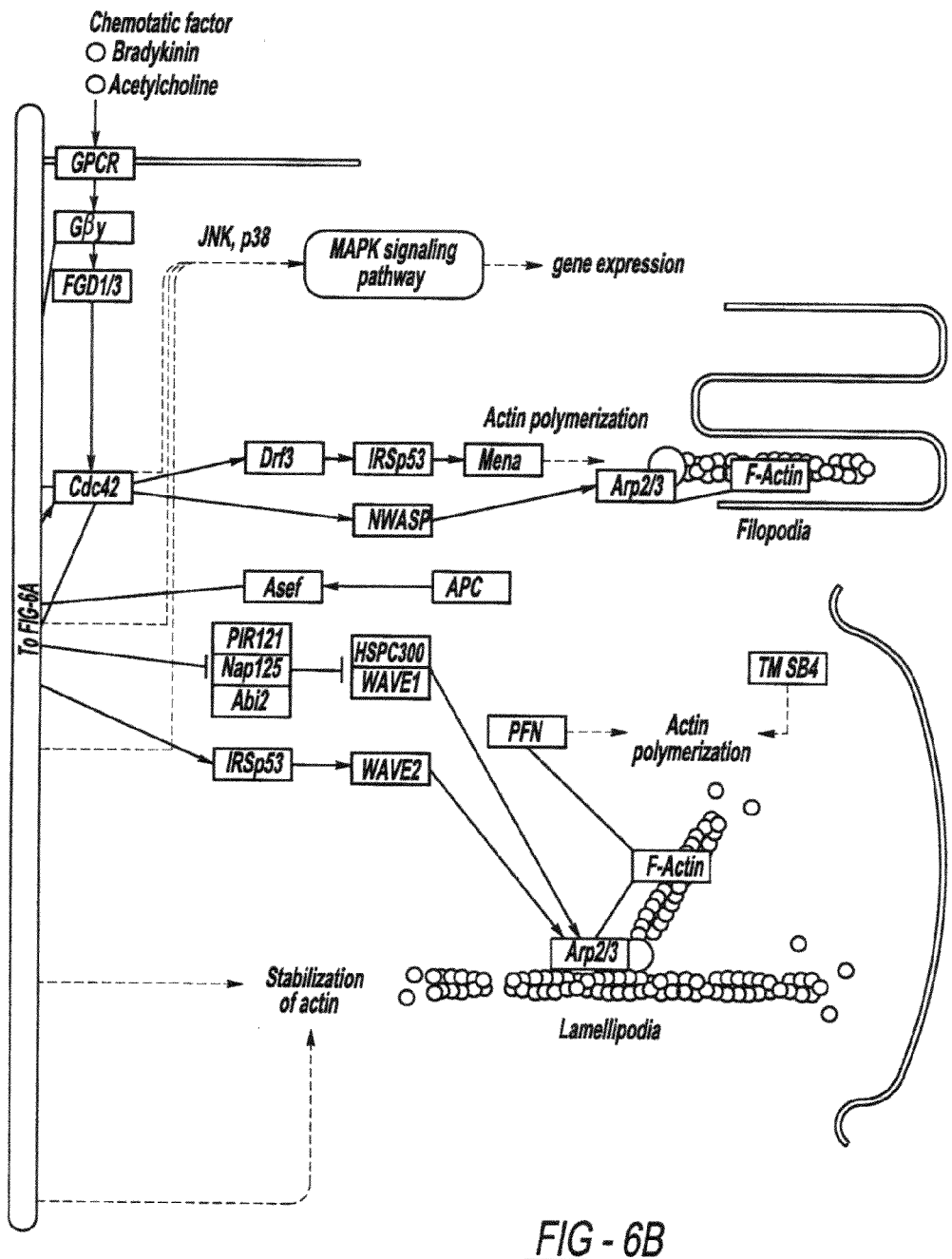

FIG. 6 depicts a actin cytoskeleton pathway in a hepatic cell line treated with palmitate. Differentially expressed genes on the actin cytoskeleton pathway are connected with arrows. For genes with no measured changes upstream, such as FN1 and CD14 (shown in blue), the gene perturbation will be equal to the measured expression change. The perturbation of genes such as ITG (shown in blue) will be higher in absolute value, reflecting both its own measured change as well as the fact that the FN1 gene immediately upstream is also differentially expressed.

Figure 7:
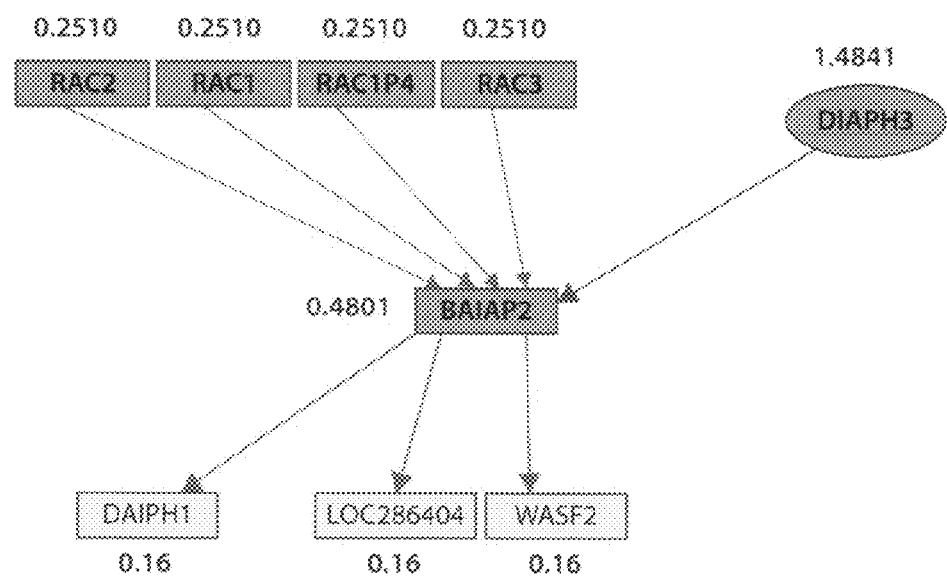

FIG. 7 illustrates a computation of the permutation factor, PF for a gene and the subsequent propagation of the perturbation according to Eq. 3. The genes are part of regulation of actin cytoskeleton pathway shown in FIG. 4. Some of the interactions between the genes have been removed in order to simplify the figure. The labels next to each gene indicate the PF and the colored genes BAIAP2 (red), DIAPH1, LOC286404 and WASF2 (yellow) and RAC2, RAC1, RACP4 and RAC3 (green) are shown to illustrate different perturbation effects propagated upstream or downstream of the genes as indicated by the colored arrows.

Figure 9B:
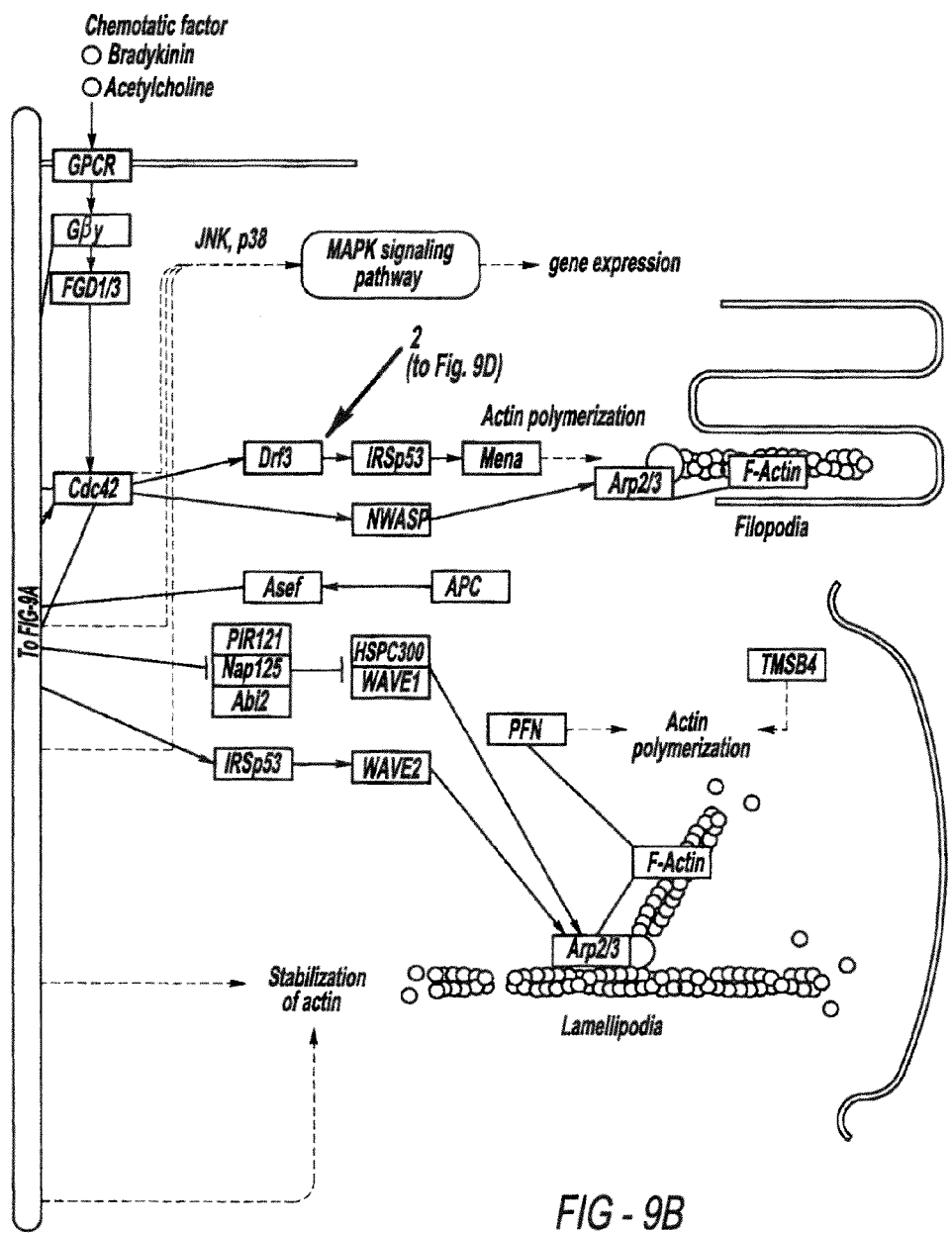
Figure 9C:
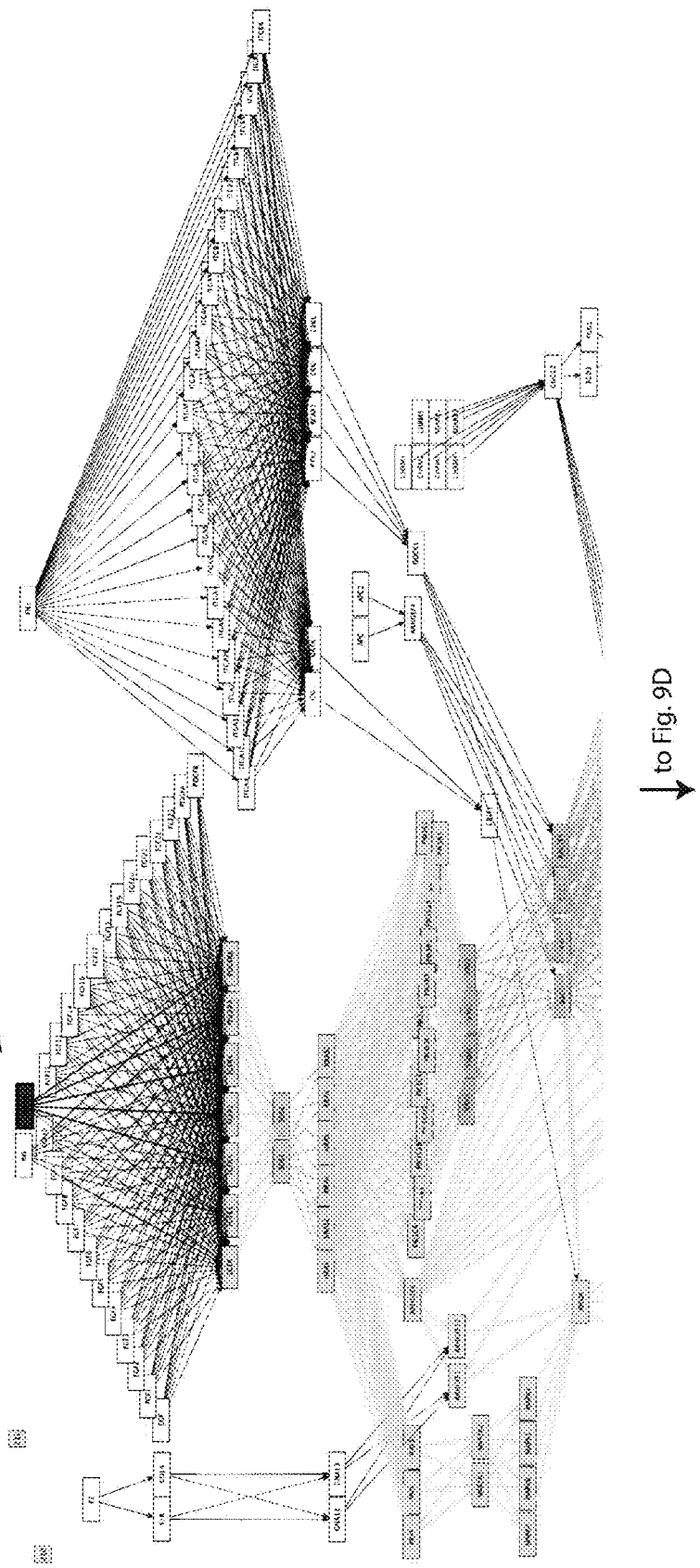
Figure 9D:
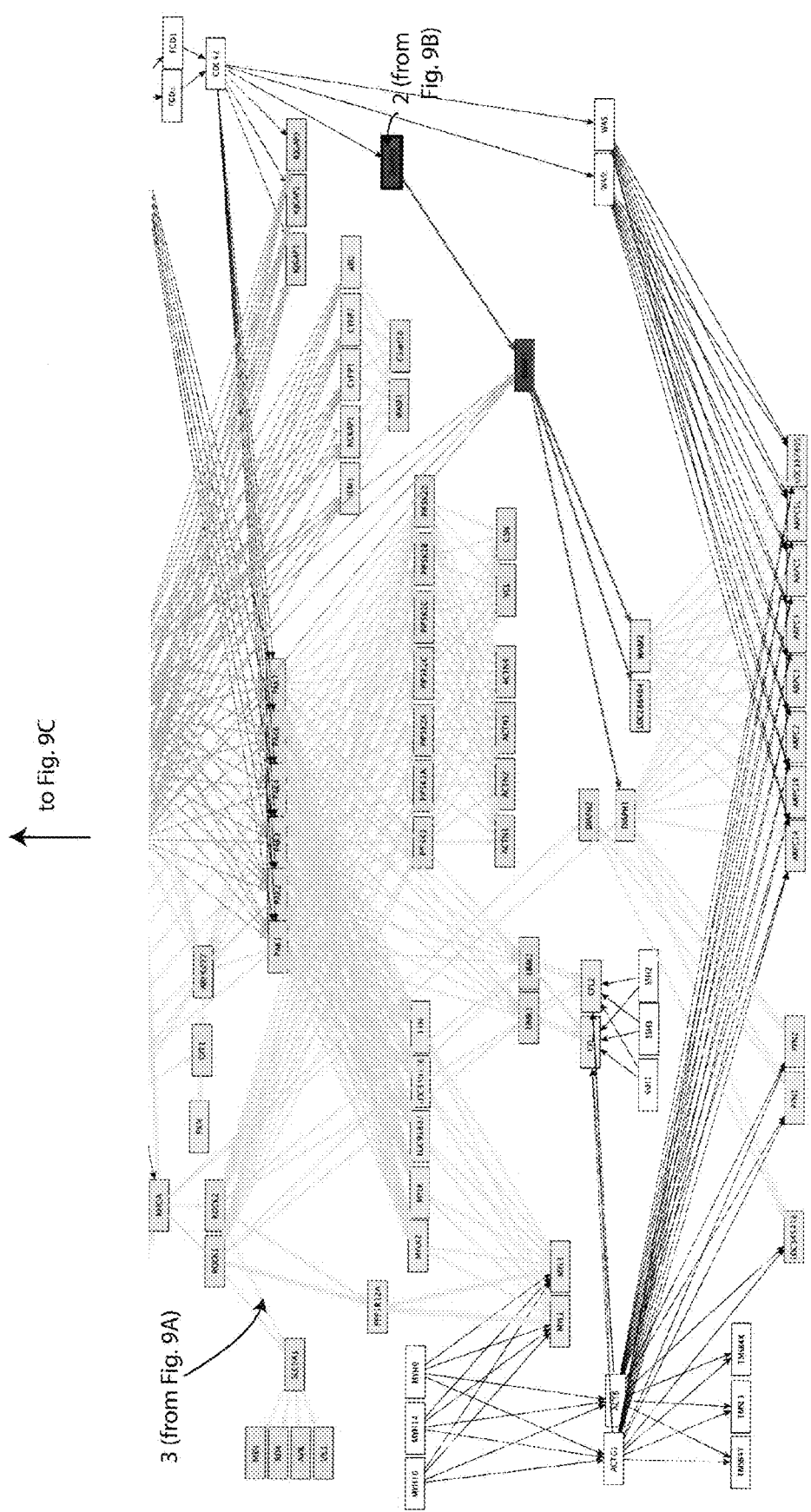

FIG. 8 depicts tabulated results of the computation and propagation of the perturbations in a small area of an actin cytoskeleton pathway (shown in its entirety in FIG. 4) using the software package "Pathway-Express" as part of "Onto-Tools" available online at http://vortex.cs.wayne.edu/Projects.html. As already mentioned, in all data shown here the regulatory efficiency is β=1 for all genes. In this case, the gene DIAPH3 is the input gene with an observed fold change ΔE=1.4841. Since there are no genes upstream of DIAPH3, its second term in Eq. 3 is zero. Using Eq. 3, the PF of gene DIAPH3 is simply its measured expression change:

FIG. 9A depicts a KEGG diagram illustrating the regulation of actin cytoskeleton as impacted in breast cancer: the KEGG pathway diagram. Note that the unique symbol GF (blue) in the KEGG diagram shown in FIG. 9A, actually stands for 25 FGF genes in the internal graph illustratively shown in FIG. 9B, only one of which is differentially expressed (1). The colors show the propagation of the gene perturbations throughout the pathway. The differentially expressed genes are FGF18 (1) and DIAPH3 (2). Arrows from FIG. 9A to FIG. 9B and vice versa are used to illustrate select gene interactions between those displayed in the KEGG pathway diagram and the internal graph represented by FIG. 9B.

FIG. 9B depicts the internal graph representation of the genes in FIG. 9A. The colored genes and colored arrows to and/or from these colored genes show the propagation of the gene perturbations throughout the pathway merely for ease of illustration depicting different classes of perturbations being propagated. The differentially expressed genes are FGF18 (blue in FIG. 9B and represented by arrow 1) and DIAPH3 (red in FIG. 9B and represented by arrow 2). Changes in the color of the arrows and genes from blue/green to yellow/red and vice versa correspond to inhibitory interactions. For instance, since ROCK inhibits MBS, the negative perturbation of ROCK propagates as a positive perturbation of MBS (3).

DETAILED DESCRIPTION

In various embodiments of the present disclosure, an impact factor (IF) is calculated for each pathway incorporating parameters such as the normalized fold change of the differentially expressed genes, the statistical significance of the set of pathway genes, and the topology of the signaling pathway. The present methods tested on a number of real data sets provide that when compared to prior art methodologies, the intrinsic limitations of the classical analysis produce both false positives and false negatives while the impact analysis of the present disclosure provides biologically meaningful results. The present disclosure provides for systems, methods, computation methods and computer readable media containing steps for developing an analysis model of biological networks including gene signaling networks and metabolic networks. In some embodiments, the present methods for analyzing a gene signaling pathway includes both a statistically significant number of differentially expressed biomolecules, (for example, genes) and biologically meaningful changes on given pathways. In this model, the impact factor (IF) of a pathway $P_i$ is calculated as the sum of two terms:

$$IF(P_i) = \log\left(\frac{1}{p_i}\right) + \frac{\sum_{g \in P_i} |PF(g)|}{|\overline{\Delta E}| \cdot N_{de}(P_i)} \quad (1)$$

The first term is a probabilistic term that captures the significance of the given pathway $P_i$ from the perspective of the set of genes contained in it. This term captures the information provided by the currently used classical statistical approaches and can be calculated using either an ORA (e.g., z-test, contingency tables, a FCS approach (e.g., GSEA) or other more recent approaches. The $p_i$ value corresponds to the probability of obtaining a value of the statistic used at least as extreme as the one observed, when the null hypothesis is true. The results shown in the present example were calculated using the hypergeometric model in which $p_i$ is the probability of obtaining at least the observed number of differentially expressed gene, $N_{de}$, just by chance.

The second term in Eq. 1 is a functional term that depends on the identity of the specific genes that are differentially expressed as well as on the interactions described by the pathway (i.e., its topology). In essence, this term sums up the absolute values of the perturbation factors (PF) for all genes g on the given pathway $P_i$. The perturbation factor of a gene g is calculated as follows:

$$PF(g) = \Delta E(g) + \sum_{u \in US_g} \beta_{ug} \cdot \frac{PF(u)}{N_{ds}(u)} \quad (2)$$

In this equation, the first term captures the quantitative information measured in the gene expression experiment. The factor $\Delta E(g)$ represents the signed normalized measured expression change of the gene g determined using one of the available methods. The second term is a sum of all perturbation factors of the genes u directly upstream of the target gene g, normalized by the number of downstream genes of each such gene $N_{ds}(u)$, and weighted by a factor $\beta_{ug}$, which reflects the type of interaction: $\beta_{ug}=1$ for induction, $\beta_{ug}=-1$ for repression. $US_g$ is the set of all such genes upstream of g. The second term here is similar to the PageRank index used by Google (Page et al., 1998) only that we weight the downstream instead of the upstream connections (a web page is important if other pages point to it whereas a gene is important if it influences other genes).

Under the null hypothesis which assumes that the list of differentially expressed genes only contains random genes, the likelihood that a pathway has a large impact factor is proportional to the number of such "differentially expressed" genes that fall on the pathway, which in turns is proportional to the size of the pathway. Thus, we need to normalize with respect to the size of the pathway by dividing the total perturbation by the number of differentially expressed genes on the given pathway, $N_{de}(P_i)$. Furthermore, various technologies can yield systematically different estimates of the fold changes. For instance, the fold changes reported by microarrays tend to be compressed with respect to those reported by RT-PCR. In order to make the impact factors as independent as possible from the technology, and also comparable between problems, we also divide the second term in Eq. 1 by the mean absolute fold change $\overline{|\Delta E|}$, calculated across all differentially expressed genes. Assuming that there are at least some differentially expressed genes anywhere in the data set, both $\overline{|\Delta E|}$ and $N_{de}(P_i)$ are different from zero so the second term is properly defined.

It can be shown that the impact factors correspond to the negative log of the global probability of having both a statistically significant number of differentially expressed genes and a large perturbation in the given pathway. Impact factor values, if, will follow a $\Gamma(2,1)$ distribution from which p-values can be calculated as: $p=(if+1)\cdot e^{-if}$ (see details in Supplementary Materials).

The impact analysis proposed here extends and enhances the existing statistical approaches by incorporating the novel aspects discussed above. For instance, the second term of the gene perturbation (Eq. 2) increases the PF scores of those genes that are connected through a direct signaling link to other differentially expressed genes (e.g., the perturbation factor of F5 and F11 in FIG. 1 are both increased because of the differentially expressed SERPINC1 and SERPINA1). This will yield a higher overall score for those pathways in which the differentially expressed genes are localized in a connected subgraph, as in this example. Interestingly, when the limitations of the existing approaches are forcefully imposed (e.g., ignoring the magnitude of the measured expression changes or ignoring the regulatory interactions between genes), the impact analysis reduces to the classical statistics and yields the same results. For instance, if there are no perturbations directly upstream of a given gene, the second term in Eq. 2 is 0, and the PF reduces to the measured expression change $\Delta E$, which is the classical way of assessing the impact of a condition upon a given gene. A more detailed discussion of various particular cases is included in the Supplementary Materials.

EXAMPLE 1

We have used this pathway analysis approach to analyze several data sets. A first such set includes genes associated with better survival in lung adenocarcinoma (Beer et al., 2002). These genes have the potential to represent an important tool for the therapeutical decision and, if the correct regulatory mechanisms are identified, they could also be potential drug targets. The expression values of the 97 genes associated with better survival identified by Beer et al. were compared between the cancer and healthy groups. These data were then analyzed using a classical ORA approach (hypergeometric model), a classical FCS approach (GSEA), and our impact analysis. FIGS. 2A-2C show the comparison between the results obtained with the 3 approaches.

From a statistical perspective, the power of both classical techniques appears to be very limited. The corrected p-values do not yield any pathways at the usual 0.01 or 0.05 significance levels, independently of the type of correction. If the significance levels were to be ignored and the techniques used only to rank the pathways, the results would continue to be unsatisfactory. According to the classical ORA analysis, the most significantly affected pathways in this data set are prion disease, focal adhesion and Parkinson's disease. In reality, both prion and Parkinson's diseases are pathways specifically associated to diseases of the central nervous system and are unlikely to be related to lung adenocarcinomas. In this particular case, prion disease ranks at the top only due to the differential expression of LAMB1. Since this pathway is rather small (14 genes), every time any one gene is differentially expressed, the hypergeometric analysis will rank it highly. A similar phenomenon happens with Parkinson's disease, indicating that this is a problem associated with the method rather than with a specific pathway. At the same time, pathways highly relevant to cancer such as cell cycle and Wnt signaling are ranked in the lower half of the pathway list. The most significant pathways reported as enriched in cancer by GSEA are: cell cycle, Huntington disease, DRPLA, Alzheimer's and Parkinson's (see FIG. 2B). Among these, only cell cycle is relevant, while Huntington's, Alzheimer's and Parkinson's are clearly incorrect. However, although ranked first, cell cycle is not significant in GSEA, even at the most lenient 10% significance and with the least conservative correction.

In contrast, the impact analysis reports cell cycle as the most perturbed pathway in this condition and also as highly significant from a statistical perspective (p=1.6·10−6 ). Since early papers on the molecular mechanisms perturbed in lung cancer, until the most recent papers on this topic, there is a consensus that the cell cycle is highly deranged in lung cancers. Moreover, cell cycle genes have started to be considered both as potential prognostic factors and therapeutic targets. The second most significant pathway as reported by the impact analysis is focal adhesion. An inspection of this pathway (shown in FIG. 3) shows that in these data, both ITG and RTK receptors are perturbed, as well as the VEGF ligand. Because these 3 genes appear at the very beginning and affect both entry points controlling this pathway, their perturbations are widely propagated throughout the pathway. Furthermore, the CRK oncogene was also found to be up-regulated. Increased levels of CRK proteins have been observed in several human cancers and over-expression of CRK in epithelial cell cultures promotes enhanced cell dispersal and invasion.

For this pathway, the impact analysis yields a raw p-value of 0.005, which remains significant even after the FDR correction (p=0.048), at the 5% level. In contrast, the ORA analysis using the hypergeometric model yields a raw p-value of 0.155 (FDR corrected to 0.627) while the GSEA analysis yields a raw p-value of 0.16 (FDR corrected to 0.384). For both techniques, not even the raw p-values are significant at the usual levels of 5% or 10%. This is not a mere accident but an illustration of the intrinsic limitations of the classical approaches. These approaches completely ignore the position of the genes on the given pathways and therefore, they are not able to identify this pathway as being highly impacted in this condition. Note that any ORA approach will yield the same results for this pathway for any set of 4 differentially expressed genes from the set of genes on this pathway. Similarly, GSEA will yield the same results for any other set of 4 genes with similar expression values (yielding similar correlations with the phenotype). Both techniques are unable to distinguish between a situation in which these genes are upstream, potentially commandeering the entire pathway as in this example, or randomly distributed throughout the pathway.

The third pathway as ranked by the impact analysis is Wnt signaling (FDR corrected p=0.055, significant at 10%). The importance of this pathway is well supported by independent research. At least three mechanisms for the activation of Wnt signaling pathway in lung cancers have been recently identified: i) over-expression of Wnt effectors such as Dvl, ii) activation of a non-canonical pathway involving JNK, and iii) repression of Wnt antagonists such as WIF-1. The present understanding with regards to Wnt signaling also suggests that the blockade of Wnt pathway may lead to new treatment strategies in lung cancer.

In the same data set, Huntington's disease, Parkinson's disease, prion disease and Alzheimer's disease have low impact factors (corrected p-values of above 0.20), correctly indicating that they are unlikely to be relevant in lung adenocarcinomas.

A second data set includes genes identified as being associated with poor prognosis in breast cancer FIGS. 4A-4C show the comparison between the classical hypergeometric approach, GSEA, and the pathway impact analysis. On this data, GSEA finds no significantly impacted pathways at any of the usual 5% or 10% levels. In fact, the only FDR-corrected value below 0.25, in the entire data set is 0.11, corresponding to the ubiquitin mediated proteolysis. Furthermore, GSEA's ranking does not appear to be useful for this data, with none of the cancer-related pathways being ranked towards the top. The most significant signaling pathway according to the hypergeometric analysis, cell cycle is also the most significant in the impact analysis. However, the agreement between the two approaches stops here. In terms of statistical power, according to the classical hypergeometric model, there are no other significant pathways at either 5% or 10% significance on the corrected p-values. If we were to ignore the usual significance thresholds and only consider the ranking, the third highest pathway according to the hypergeometric model is Parkinson's disease. In fact, based on current knowledge, Parkinson's disease is unlikely to be related to rapid metastasis in breast cancer. At the same time, the impact analysis finds several other pathways as significant. For instance, focal adhesion is significant with an FDR-corrected p-value of 0.03. In fact, a link between focal adhesion and breast cancer has been previously established. In particular, FAK, a central gene on the focal adhesion pathway, has been found to contribute to cellular adhesion and survival pathways in breast cancer cells which are not required for survival in non-malignant breast epithelial cell. Recently, it has also been shown that Doxorubicin, an anti-cancer drug, caused the formation of well defined focal adhesions and stress fibers in mammary adenocarcinoma MTLn3 cells early after treatment. Consequently, the FAK/PI-3 kinase/PKB signaling route within the focal adhesion pathway has been recently proposed as the mechanism through which Doxorubicin triggers the onset of apoptosis.

TGF-beta signaling (p=0.032) and MAPK (p=0.064) are also significant. Both fit well with previous research results. TGF-beta1, the main ligand for the TGF-beta signaling pathway, is known as a marker of invasiveness and metastatic capacity of breast cancer cells. In fact, it has been suggested as the missing link in the interplay between estrogen receptors and HER-2 (human epidermal growth factor receptor 2). Furthermore, plasma levels of TGF-beta1 have been used to identify low-risk postmenopausal metastatic breast cancer patients. Finally, MAPK has been shown to be connected not only to cancer in general, but to this particular type of cancer. For instance the proliferative response to progestin and estrogen was shown to be inhibited in mammary cells microinjected with inhibitors of MAP kinase pathway. Also, it is worth noting the gap between the p-values for regulation of actin cytoskeleton (p=0.111), which may be relevant in cancer, and the next pathway, Parkinson's disease (p=0.239), which is irrelevant in this condition.

A third data set involves a set of differentially expressed genes obtained by studying the response of a hepatic cell line when treated with palmitate. FIGS. 5A and 5B show the comparison between the classical statistical analysis (ORA) and the pathway impact analysis. The classical statistical analysis yields 3 pathways significant at the 5% level: complement and coagulation cascades, focal adhesion and MAPK. The impact analysis agrees on all these, but also identifies several additional pathways. The top 4 pathways identified by the impact analysis are well supported by the existing literature. There are several studies that support the existence of a relationship between different coagulation factors, present in the complement and coagulation cascades pathway, and palmitate. It has also been demonstrated that a high palmitate intake affects factor VII coagulant (FVIIc) activity. Interestingly, FIG. 1 shows not only that this pathway has a higher than expected proportion of differentially expressed genes, but also that 6 out of 7 such genes are involved in the same region of the pathway, suggesting a coherently propagated perturbation. The focal adhesion and tight junction pathways involve cytoskeletal genes. Others have considered the presence of the cytoskeletal genes among the differentially expressed genes as very interesting and hypothesized that the down-regulation of these cytoskeletal genes indicates that palmitate decreases cell growth. Finally, the link between MAPK and palmitate has been established indicating that p38 MAP kinase is a key player in the palmitate-induced apoptosis.

A statistical approach using various models is commonly used in order to identify the most relevant pathways in a given experiment. This approach is based on the set of genes involved in each pathway. We identified a number of additional factors that may be important in the description and analysis of a given biological pathway. Based on these, we developed a novel impact analysis method that uses a systems biology approach in order to identify pathways that are significantly impacted in any condition monitored through a high throughput gene expression technique. The impact analysis incorporates the classical probabilistic component but also includes important biological factors that are not captured by the existing techniques: the magnitude of the expression changes of each gene, the position of the differentially expressed genes on the given pathways, the topology of the pathway which describes how these genes interact, and the type of signaling interactions between them. The results obtained on several independent data sets show that the proposed approach is very promising. This analysis method has been implemented as a web-based tool, Pathway-Express, freely available as part of the Onto-Tools software package. (Wayne State University, Detroit, Mich., USA).

The approach proposed here evaluates the strength of the null hypothesis $H_0$ (that the pathway is not significant), by combining two types of evidence. In a first analysis, a classical over-representation analysis (ORA) approach provides a p-value defined as the probability that the number of differentially expressed genes, X, is larger than or equal to the observed number of differentially expressed genes, $N_{de}$, just by chance (when the null hypothesis $H_0$ is true):

$$p_i = P(X \geq N_{de} | H_0) \quad (3)$$

Next, in a separate perturbation analysis, the impact of topology, gene interactions, and gene fold changes come into play and are captured thought the pathway perturbation factor:

$$PF = \frac{\sum_{g \in P_i} |PF(g)|}{|\overline{\Delta E}| \cdot N_{de}(P_i)} \quad (4)$$

where $N_{de}$ (Pi) is the number of differentially expressed genes on the given pathway $P_i$, PF (g) is the perturbation of the gene g:

$$PF(g) = \Delta E(g) + \sum_{u \in US_g} \beta_{ug} \cdot \frac{PF(u)}{N_{ds}(u)} \quad (5)$$

and $\Delta E$ is the mean fold change over the entire set of N differentially expressed genes:

$$|\overline{\Delta E}| = \frac{\sum_{k=1}^{N} |\Delta E|}{N} \quad (6)$$

Let PF denote the perturbation factor as a random variable and pf be the observed value for a particular pathway. The score pf is always positive, and the higher its value, the less likely the null hypothesis (that the pathway is not significant). Moreover this likelihood decays very fast as pf gets away from zero. These features point to the exponential distribution as an appropriate model for the random variable PF. Under the null hypothesis, differentially expressed genes would fall on the pathway randomly, and would not interact with each other in any concerted way. In other words, in the second term in Eq. 5 (which captures the influence of the genes upstream) roughly half of those influences will be positives, and half negative, canceling each other out. In such circumstances, the perturbation of each gene would be limited to its own measured fold change (due to random unrelated causes):

$$PF(g) = \Delta E(g) + \sum_{u \in US_g} \beta_{ug} \cdot \frac{PF(u)}{N_{ds}(u)} \quad (7)$$

$$= \Delta E(g) + 0$$

$$= \Delta E(g)$$

Consequently, under the same null hypothesis, the expected value for the perturbation of a pathway (from Eq. 4) will be:

$$E(PF) = E\left(\frac{\sum_{g \in P_i} |PF(g)|}{|\overline{\Delta E}| \cdot N_{de}(P_i)}\right) \quad (8)$$

$$= E\left(\frac{1}{|\overline{\Delta E}|} \frac{\sum_{k=1}^{N_{de}(P_i)} |\Delta E(g)|}{N_{de}(P_i)}\right)$$

$$= E\left(\frac{|\overline{\Delta E_{P_i}}|}{|\overline{\Delta E}|}\right)$$

$$= 1$$

The last fraction above is the ratio between the mean fold change on the given pathway, Pi, and the mean fold change in the entire data set. Under the null hypothesis, the genes are distributed randomly across pathways and the two means should be equal. Since this expected value is 1, the distribution of the random variable PF can be modeled by the exponential of mean 1, exp(1).

If we use the PF score as a test statistics and assume its null distribution is exponential with mean 1, then the p-value $p_{pf}$ resulting from the perturbation analysis will have the form:

$$p_{pf} = P(PF \geq pf | H_0) = e^{-pf} \quad (9)$$

This is the probability of observing a perturbation factor, PF, greater or equal to the one observed, pf, when the null hypothesis is true.

Let us now consider that for a given pathway we observe a perturbation factor equal to pf and a number of differentially expressed genes equal to $N_{de}$. A 'global' probability $p_{global}$, of having just by chance both a higher than expected number of differentially expressed genes AND a significant biological perturbation (large PF in the second term), can be defined as the joint probability:

$$p_{global} = P(X \geq N_{de}, PF \geq pf | H_0) \quad (10)$$

Since the pathway perturbation factor in Eq. (4) is calculated by dividing the total pathway perturbation by the number of differentially expressed genes on the given pathway, the PF will be independent of the number of differentially expressed genes X, and the joint probability above becomes a product of two single probabilities:

$$p_{global} = P(X \geq N_{de} | H_0) \cdot P(PF \geq pf | H_0) \quad (11)$$

This $p_{global}$ provides a global significance measure that requires both a statistically significant number of differentially expressed genes on the pathway, $N_{de}$, and at the same time, large perturbations on the same pathway as described by pf. Using equations (3) and (9), the formula (11) becomes:

$$p_{global} = p_i \cdot e^{-pf} \quad (12)$$

We take a natural log of both sides and obtain:

$$-\log(p_{global}) = -\log(p_i) + pf \quad (13)$$

which can be re-written as:

$$-\log(p_{global}) = -\log(p_i) + pf \quad (14)$$

in which we can substitute the definition of pf from (4) above to yield:

$$-\log(p_{global}) = -\log(p_i) + PF \quad (15)$$

The right hand side of this expression is exactly our definition of the impact factor:

$$IF = -\log(p_i) + \frac{\sum_{g \in P_i} |PF(g)|}{|\overline{\Delta E}| \cdot N_{de}(P_i)} \quad (16)$$

This shows that the proposed impact factor, IF, is in fact the negative log of the global probability of having both a statistically significant number of differentially expressed genes and a large perturbation in the given pathway.

Ignoring the discrete character of the hypergeometric distribution, under the null hypothesis $p_i = P(X \geq N_{RP} H_0)$ has a uniform distribution. By taking negative log, the distribution changes into exponential with parameter 1, similar to the distribution we assumed for PF, the second term in IF formula.

$$-\log(p_i) \sim \exp(1); PF \sim \exp(1); \exp(1) = \Gamma(1,1) \quad (17)$$

Then, as the sum of two independent exponential random terms, the IF will follow a Gamma distribution $\Gamma(2, 1)$. The pdf of this distribution is:

$$f(x) = xe^{-x}, x \geq 0 \quad (18)$$

Finally, the p-value corresponding to the observed value if of the statistic IF can be easily computed by integrating the density (16):

$$p = P(IF \geq if \mid H_0) \quad (19)$$
$$= \int_{if}^{\infty} f(x) \, dx$$
$$= \int_{if}^{\infty} xe^{-x} \, dx$$
$$= (if + 1) * e^{-if}$$

The impact analysis proposed includes and extends the classical approach both with respect to individual genes and with respect to pathways. We discuss briefly a few interesting particular cases. These cases illustrate how, when the limitations of the classical approach are forcefully imposed (e.g., ignoring the magnitude of the measured expression changes or ignoring the regulatory interactions between genes), the impact analysis reduces to the classical approach and yields the same results.

In our analysis, the gene perturbation factor for a gene g is defined as:

$$PF(g) = \Delta E(g) + \sum_{u \in US_g} \beta_{ug} \cdot \frac{PF(u)}{N_{ds}(u)} \quad (5)$$

If there are no measured differences in the expression values of any of the genes upstream of g, PF (u)=0 for all genes in $US_g$, and the second term becomes zero. In this case the perturbation factor reduces to:

$$PF(g) = \Delta E \quad (20)$$

This is exactly the classical approach, in which the amount of perturbation of an individual gene in a given condition is measured through its expression change $\Delta E$. Examples could include the genes FN1 and CD14 in FIG. 6.

The pathway analysis framework can also be used in the framework in which the ORA approach is usually used. If the expression changes measured for the pathway genes are to be ignored (as they are in the ORA approach), the pathway impact analysis can still be used to assess the impact of a condition upon specific pathways. This is achieved by setting all measured expression changes $\Delta E(g)=0$ for all genes on the given pathway $g \in P_i$. This will make all gene perturbation factors zero:

$$PF(g) = \Delta E(g) + \sum_{u \in US_g} \beta_{ug} \cdot \frac{PF(u)}{N_{ds}(u)} = 0 \quad (21)$$

Assuming that there are at least some differentially expressed genes somewhere in this data set[a], (i.e. $\Delta E = 0$) the pathway impact factor in Eq. 16 becomes:

$$IF(P_i) = \log\left(\frac{1}{p_i}\right) + \frac{\sum_{g \in P_i} |PF(g)|}{|\overline{\Delta E}| \cdot N_{de}(P_i)} \quad (22)$$
$$= \log\left(\frac{1}{p_i}\right) + 0$$
$$= -\log(p_i)$$

Since the expression now involves a single random variable, the IF values will follow a $\Gamma(1, 1) = \exp(1)$, rather than a $\Gamma(2, 1)$ distribution, and our p value can be calculated as:

$$p = P(IF \geq -\log(p_i) \mid H_0) \quad (23)$$
$$= \int_{-\log(p_i)}^{\infty} e^{-x} \, dx$$
$$= -e^{-x} \big|_{-\log(p_i)}^{\infty}$$
$$= e^{\log(p_i)}$$
$$= p_i$$

This expression shows that in this particular case, the impact analysis reduces to exactly the classical approach which measures the impact of a pathway by looking exclusively at the probability of the given number of differentially expressed genes occurring just by chance, i.e., the p-value yielded by an analysis in which only the set of genes is considered.

It is entirely possible that certain genes are in fact changing their expression level but the change is below the sensitivity threshold of the technology, or below the threshold used to select differentially expressed genes. It is also possible that the regulation between genes happens at levels other than that of the mRNA (e.g., phosphorylation, complex formation, etc.). Hence, signals should be allowed to be propagated around the pathway even through those genes for which no expression change has been detected at the mRNA level. The perturbation factor model accounts for these situations. If the measured expression change is zero, the perturbation of the gene becomes:

$$PF(g) = \sum_{u \in US_g} \beta_{ug} \cdot \frac{PF(u)}{N_{ds}(u)} \quad (24)$$

In this case, the perturbation of a given gene is due to the perturbations of the genes upstream, propagated through the pathway topology.

In certain situations, one might not wish that the analysis propagate the gene perturbations through specific graph edges or types of graph edges (e.g., for edges corresponding to indirect effects or state changes). This can be easily achieved by setting $\beta=0$ for the desired edges or edge types.

If no perturbation propagations are to be allowed at all, the expression of the gene perturbation in Eq. 5 reduces to:

$$PF(g) = \Delta E \quad (25)$$

and the impact factor for the pathway becomes:

$$IF(P_i) = \log\left(\frac{1}{p_i}\right) + \frac{\sum_{g \in P_i} |PF(g)|}{|\overline{\Delta E}| \cdot N_{de}(P_i)} \quad (26)$$

$$= \log\left(\frac{1}{p_i}\right) + \frac{1}{|\overline{\Delta E}|} \frac{\sum_{k=1}^{N_{de}(P_i)} |\Delta E(g)|}{N_{de}(P_i)}$$

$$= \log\left(\frac{1}{p_i}\right) + \frac{|\overline{\Delta E_{P_i}}|}{|\overline{\Delta E}|}$$

In this case, the impact analysis would assess the pathways based not only on the number of differentially expressed genes that fall on each pathway but also based on the ratio between the average expression change on the pathway and the average expression change in the entire set of differentially expressed genes.

FIG. 7 illustrates the computation and propagation of the perturbations in a small area of an actin cytoskeleton pathway (shown in its entirety in FIGS. 9A and 9B). As already mentioned, in all data shown here the regulatory efficiency is $\beta=1$ for all genes. In this case, the gene DIAPH3 is the input gene with an observed fold change $\Delta E=1.4841$. Since there are no genes upstream of DIAPH3, its second term in Eq. 5 is zero. Using Eq. 5, the PF of gene DIAPH3 is simply its measured expression change:

$$PF(DIAPH3) = 1.4841 + 0 = 1.4841 \quad (26)$$

The next step involves the computation of the perturbation for BAIAP2. This gene receives signals from DIAPH3 but also from RAC1, RAC1P4, RAC2 and RAC3. Using Eq. 5, the PF for the gene BAIAP2 can be calculated as:

$$PF(BAIAP2) = \Delta E(BAIAP2) + \frac{PF(DIAPH3)}{N_{ds}(DIAPH3)} +$$

$$\frac{PF(RAC1)}{N_{ds}(RAC1)} + \frac{PF(RAC1P4)}{N_{ds}(RAC1P4)} + \frac{PF(RAC2)}{N_{ds}(RAC2)} + \frac{PF(RAC3)}{N_{ds}(RAC3)}$$

The previously calculated perturbations for RAC1, RAC1P4, RAC2 and RAC3 are:

$$PF(RAC1) = PF(RAC1P4) = PF(RAC2) = PF(RAC3) = -0.251 \quad (27)$$

Each of these genes signals only to BAIAP2 so for each of them the number of downstream genes, $N_{ds}$ will be equal to 1. Hence, the PF for the gene BAIAP2 can be calculated as:

$$PF(BAIAP2) = 1.4841 + \frac{-0.251}{1} + \frac{-0.251}{1} + \quad (28)$$

$$\frac{-0.251}{1} + \frac{-0.251}{1}$$

$$= 0.4801$$

Similarly, using Eq. 5, the PF for the gene DIAPH1 is $$PF(DIAPH1) = \Delta E(DIAPH1) + \frac{PF(BAIAP2)}{N_{ds}(BAIAP2)} \quad (29)$$

$$= 0 + \frac{0.4801}{3}$$

$$= 0.16$$

The perturbation of the other two genes, LOC286404 and WASF2 is analogous and yields the same numerical value.

If the pathway includes loops, Eq. 5 becomes recursive, and the computation of the gene PFs will involve an iterative process. The best way of treating such loops would probably involve modeling the pathways as dynamical systems and using differential (or difference) equations to study them from the point of view of stability and convergence. However, at the moment, the expression data generated by the currently available techniques do not appear to be sufficiently accurate to allow this type of analysis. The very same biological samples analyzed on various platforms yield numbers that often correlate only around 0.7. Treating the pathways as dynamical systems with such data runs quickly into stability problems. In order to address this in a feasible way, we perform the computation of the perturbation factors by going around each loop once. This approach appears to be a good compromise for the nature of the data: loops are not completely ignored and, at the same time, stability problems created by noisy data are avoided. The drawback is that the impact factor can only be interpreted in a probabilistic framework, and cannot be put into any type of quantitative correspondence with any biochemical product anywhere on the pathway.

The typical output window using the methods of the present disclosure is shown in FIG. 8. The tool uses pathway data from KEGG and implements both the classical statistical approach (ORA), as well as the impact analysis described above, allowing a side by side comparison. The tool also allows rapid queries for genes or pathways, visualization of entire pathways (see FIG. 6), etc.

Currently, all signaling pathways for human, mouse and rat are downloaded from KEGG and stored in a relational database. In order to calculate the impact factor for a given pathway, the pathway database is queried to retrieve all genes and gene interactions in the pathway, and a graph data structure for this pathway is created. The genes are represented as nodes, and the gene interactions as edges of the graph (see FIGS. 9A and 9B). The user-provided normalized fold changes are mapped on the pathway graph and used to calculate the gene perturbation factors as described in Eq. 5. Once the perturbation factors of all genes in a given pathway are calculated, Eq. 16 is used to calculate the impact factor of each pathway. The impact factor of each pathway is then used as a score to assess the impact of a given gene expression data set on all pathways (the higher the impact factor, the more significant the pathway).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A method for predicting the significance of a biological pathway in a disease state, comprising:
   (a) providing data on the expression levels of a plurality of biomolecules differentially expressed in a disease state as compared with the same biomolecules expressed in a non-disease state within said pathway;
   (b) determining the probability of the presence of said plurality of biomolecules in said diseased state;
   (c) determining the effect of each biomolecule from said plurality of biomolecules on the expression of different downstream biomolecules within said pathway thereby providing a perturbation factor for each biomolecule in said pathway;
   (d) combining the statistical significance of said differentially expressed biomolecules within said pathway present in said disease state with a sum of perturbation factors for all of the biomolecules in said pathway to generate an impact factor for said pathway;
   (e) calculating a statistical significance of said impact factor based upon a determined probability of having a statistical significant presence of differentially expressed biomolecules in step (b) and the sum of perturbation factors within said pathway in step (c); and
   (f) outputting said statistical significance of said impact factor for said pathway relevant to said disease for a user.

2. The method of claim 1, wherein the biomolecule is a gene.

3. The method of claim 1, wherein the biomolecule is a mammalian metabolite.

* * * * *